US008637665B2

(12) United States Patent
Ahmed et al.

(10) Patent No.: US 8,637,665 B2
(45) Date of Patent: Jan. 28, 2014

(54) PYRROLO[2,L-C][L,4]BENZODIAZEPINE-BENZOTHIAZOLE OR BENZOXAZOLE CONJUGATES LINKED THROUGH PIPERAZINE MOIETY AND PROCESS FOR THE PREPARATION THEREOF

(75) Inventors: Kamal Ahmed, Hyderabad (IN); Rajesh V. C. R. N. C. Shetti, Hyderabad (IN); K. Srinivasa Reddy, Hyderabad (IN); Adla Malla Reddy, Hyderabad (IN); Ponnampally Swapna, Hyderabad (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 13/525,555

(22) Filed: Jun. 18, 2012

(65) Prior Publication Data
US 2012/0316335 A1    Dec. 13, 2012

Related U.S. Application Data

(63) Continuation of application No. PCT/IN2011/000181, filed on Mar. 18, 2011.

(30) Foreign Application Priority Data

Mar. 22, 2010    (IN) .............................. 683/DEL/2010

(51) Int. Cl.
*C07D 487/04*    (2006.01)
(52) U.S. Cl.
USPC ........................................................ 540/496
(58) Field of Classification Search
USPC ........................................................ 540/496
See application file for complete search history.

(56) References Cited

U.S. PATENT DOCUMENTS 6,979,684 B1    12/2005    Kamal et al.

FOREIGN PATENT DOCUMENTS

WO    2008099416 A2    8/2008

OTHER PUBLICATIONS

Kaplan, et al.; "Anthramycin Binding to Deoxyribonucleic Acid-Mitomycin C Complexes. Evidence for Drug-Induced Deoxyribonucleic Acid Conformational Change and Cooperativity in Mitomycin C Binding"; Biochemistry 1981, 20, pp. 7572-7580.
Hutchinson, et al.; "Antitumor Benzothiazoles. 14.1 Synthesis and in Vitro Biological Properties of Fluorinated 2-(4-Aminophenyl)benzothiazoles"; J. Med. Chem. 2001, 44, pp. 1446-1455.
Mortimer, et al.; "Antitumor Benzothiazoles. 26.1 2-(3,4-Dimethoxyphenyl)-5-fluorobenzothiazole (GW 610, NSC 721648), a Simple Fluorinated 2-Arylbenzothiazole, Shows Potent and Selective Inhibitory Activity against Lung, Colon, and Breast Cancer Cell Lines"; J. Med. Chem. 2006, 49, pp. 179-185.
Shi, et al.; "Antitumor Benzothiazoles. 3.1 Synthesis of 2-(4-Aminophenyl)benzothiazoles and Evaluation of Their Activities against Breast Cancer Cell Lines in Vitro and in Vivo"; J. Med. Chem. 1996, 39, pp. 3375-3384.
Kashiyama, et al.; "Antitumor Benzothiazoles. 8.1 Synthesis, Metabolic Formation, and Biological Properties of the C- and N-Oxidation Products of Antitumor 2-(4-Aminophenyl)-benzothiazoles"; J.Med. Chem. 1989, 424, pp. 4172-4184.
Plunkett, et al.; "Comparison of the Activity of 2•-Deoxycoformycin and Erythro-9-(2-Hydroxy-3-Nonyl)Adenine In Vivo"; Biochemical Pharmacology. vol. 28. pp. 201-206 © Pergamon Press Ltd. 1979.
Dervan; "Design of Sequence-Specific DNA-Binding Molecules"; Science vol. 232; Apr. 25, 1986; pp. 464-471.
Gregson, et al.; "Design, Synthesis, and Evaluation of a Novel Pyrrolobenzodiazepine DNA-Interactive Agent with Highly Efficient Cross-Linking Ability and Potent Cytotoxicity"; J. Med. Chem. 2001, 44, pp. 737-748.
Kamal, et al.; "Design, Synthesis, and Evaluation of New Noncross-Linking Pyrrolobenzodiazepine Dimers with Efficient DNA Binding Ability and Potent Antitumor Activity"; J. Med. Chem. 2002, 45, pp. 4679-4688.
Hurley; "DNA and Associated Targets for Drug Design"; Journal of Medicinal Chemistry; vol. 32, No. 9, Sep. 1989; pp. 2027-2033.
International Preliminary Report on Patentability Application No. PCT/IN2011/000181 Completed: Apr. 10, 2012 20 pages.
International Search Report & Written Opinion of the International Searching Authority Application No. PCT/IN2011/000181 Completed: Jun. 16, 2011; Mailing Date: Jul. 1, 2011 8 pages.
Kohn, et al.; "Reaction of Anthramycin with Deoxyribonucleic Acid"; J. Mol. Biol. (1970) 51, pp. 551-572.
Kumar, et al.; "Synthesis and Evaluation of Anticancer Benzoxazoles and Benzimidazoles Related to UK-1"; Bioorganic & Medicinal Chemistry 10 (2002) pp. 3997-4004.
Gong, et al.; "Synthesis and SAR of 2-arylbenzoxazoles, benzothiazoles and benzimidazoles as inhibitors of lysophosphatidic acid acyltransferase-β"; Bioorganic & Medicinal Chemistry Letters 14 (2004) pp. 1455-1459.
Thurston, et al.; "Synthesis of DNA-Interactive Pyrrole[ 2,I-c][ 1,4]benzodiazepines"; Chem. Rev. 1994, 94, pp. 433-465.
Molina, et al.; "Synthesis of Pyrrolo[2,1-c][1,4]benzodiazepines via an Intramolecular Aza-Wittig Reaction. Synthesis of the Antibiotic DC-81"; Tetrahedron vol. 51, No. 19, pp. 5617-5630, 1995.
Kamal, et al.; "Synthesis of Pyrrolo[2,1-c][1,4]benzodiazepine Antibiotics via Azido Reductive Cydization with HMDST"; Tetrahedron Letters, vol. 37, No. 37. pp. 6803-6806; 1996.
Thurston, et al.; "Synthesis of Sequence-Selective C8-Linked Pyrrolo[2,1-c][1,4] benzodiazepine DNA Interstrand Cross-Linking Agents"; J. Org. Chem. 1996, 61, pp. 8141-8147.

*Primary Examiner* — Bruck Kifle
(74) *Attorney, Agent, or Firm* — St. Onge Steward Johnston & Reens LLC

(57) ABSTRACT

A compound of general formula 9, useful as potential antitumor agents against human cancer cell line and a process for the preparation of Pyrrolo[2,1-c] [1,4]benzodiazepine-benzothiazole or benzoxazole conjugates linked through piperazine of general formula 9 wherein: R, $R_1$=H, F, $OCF_3$, Cl, OMe; $R_2$=OCH3 or H; $n_1$ $n_2$=3, 4; x=S or O.

3 Claims, 3 Drawing Sheets

PYRROLO[2,L-C][L,4]BENZODIAZEPINE-BENZOTHIAZOLE OR BENZOXAZOLE CONJUGATES LINKED THROUGH PIPERAZINE MOIETY AND PROCESS FOR THE PREPARATION THEREOF

CROSS-REFERENCE TO RELATED APPLICATIONS

The present application is a continuation of pending International patent application PCT/IN2011/000181 filed on Mar. 18, 2011 which designates the United States and claims priority from Indian patent application 683/DEL/2010 filed on Mar. 22, 2010.

FIELD OF THE INVENTION

The present invention relates to Pyrrolo[2,1-c][1,4]benzodiazepine-benzothiazole or benzoxazole conjugates linked through piperazine moiety of general formula 9 as potential antitumour agent.

GENERAL FORMULA 9

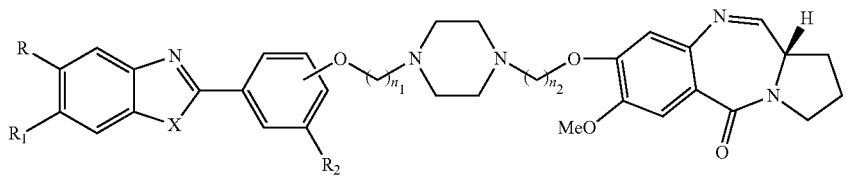

Wherein: R, $R_1$=H, F, $OCF_3$, $CF_3$, Cl or OMe;
$R_2$=$OCH_3$ or H;
$n_1$, $n_2$=3 or 4;
X=S or O.

Present invention also further relates to a process for the preparation of Pyrrolo[2,1-c][1,4]benzodiazepine-benzothiazole or benzoxazole conjugates linked through piperazine moiety.

The present invention further relates to a process for the preparation of 7-Methoxy-8-[$n_2$-(4-{$n_1$-[3 or 4(1,3-benzothiazol-2-yl)-substitutedphenoxy]alkyl}piperazin-1-yl)alkyl]oxy-(11aS)-1,2,3, 11a-tetrahydro-5H-pyrrolo[2,1-c][1,4]benzodiazepin-5-one and 7-Methoxy-8-[$n_2$-(4-{$n_1$-[3 or 4(1,3-benzoxazol-2-yl)-substitutedphenoxy]alkyl}piperazin-1-yl)alkyl]oxy-(11aS)-1,2,3, 11a-tetrahydro-5H-pyrrolo [2,1-c][1,4]benzodiazepin-5-one with aliphatic chain length variations.

BACKGROUND OF THE INVENTION

Pyrrolo[2,1-c][1,4]benzodiazepines (PBDs), a group of potent naturally occurring antitumour antibiotics from various *Streptomyces* species, are of considerable interest because of their ability to recognize and subsequently form covalent bonds to specific base sequence of double strand DNA (Dervan, P. B. *Science* 1989, 232, 464.; Hurley, L. H. *J. Med. Chem.* 1989, 32, 2027.; Thurston, D. E.; Thompson, A. S.*Chem. Br.* 1990, 26, 767). Well-known members of this group include anthramycin, DC-81, sibiromycin, tomamycin, chicamycin and neothramycin of A and B (Hurley, L. H. *J. Antibiot.* 1977, 30, 349.; Schimizu, K.; Kawamoto, I.; Tomita, F.; Morimoto, M.; Fujimoto, K. *J. Antibiot* 1982, 35, 992.; Lown, J. W.; Joshua, A. V. *Biochem. Pharmacol.* 1979, 28, 2017.; Thurston, D. E.; Bose, D. S. *Chem. Rev.* 1994, 94, 433.; Molina, P.; Diaz, I.; Tarraga, A. *Tetrahedron* 1995, 51, 5617.; Kamal, A.; Rao, N. V. *Chem. Commun.* 1996, 385.; Kamal, A.; Reddy, B. S. P.; Reddy, B. S. N. *Tetrahedron Lett.* 1996, 37, 6803). The cytotoxicity and antitumour activity of these agents are attributed to their property of sequence selective covalent binding to the N2 of guanine in the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot,* 1980, 33, 665.; Kohn, K. W. and Speous, C. L. *J. Mol. Biol.,* 1970, 51, 551.; Hurley, L. H.; Gairpla, C. and Zmijewski, M. *Biochem. Biophys. Acta.,* 1977, 475, 521.; Kaplan, D. J. and Hurley, L. H. *Biochemistry,* 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C; Neidle, S. and Hurley, L. H. *J. Org. Chem.* 1996, 61, 8141).

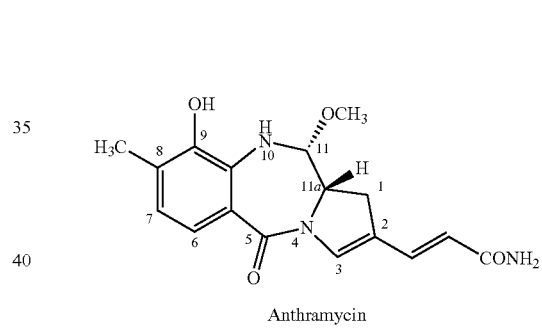

Anthramycin

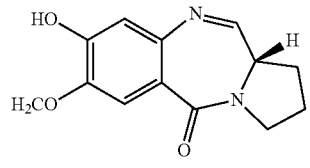

DC-81

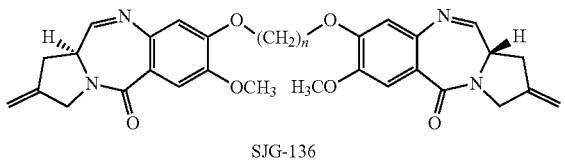

SJG-136

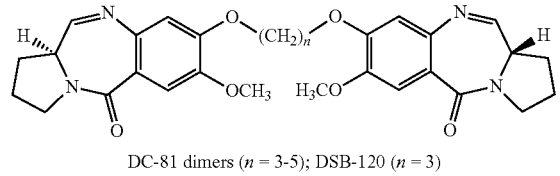

DC-81 dimers (*n* = 3-5); DSB-120 (*n* = 3)

-continued

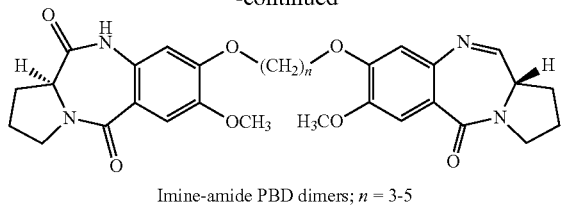

Imine-amide PBD dimers; n = 3-5

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). However, the clinical efficacy for these antibiotics is hindered by several limitations, such as poor water solubility, cardiotoxicity, development of drug resistance and metabolic inactivation. Due to the excellent activity of these molecules, there is need to develop novel derivatives which are devoid of above limitations.

Benzothiazoles are small synthetic molecules that contain a benzene ring fused to a thiazole ring. These simple molecules have shown remarkable antitumour properties and some of them are undergoing evaluation in clinical trials (Shi, D. -F.; Bradshaw, T. D.; Wrigley, S.; McCall, C. J.; Lelieveld, P.; Fichtner, I.; Stevens, M. F. G. *J. Med. Chem.* 1996, 39, 3375; Kashiyama, E.; Hutchinson, I.; Chua, M. -S.; Stinson, S. F.; Phillips, L. R.; Kaur, G.; Sausville, E. A.; Bradshaw, T. D.; Westwell, A. D.; Stevens, M. F. G. *J. Med. Chem.* 1999, 42, 4172; Hutchinson, I.; Chua, M. -S.; Browne, H. L; Trapani, V.; Bradshaw, T. D.; Westwell, A. D.; Stevens, M. F. G. *J. Med. Chem.* 2001, 44, 1446). Recently Westwell and coworkers have prepared a series of benzothiazole derivatives and evaluated for anticancer activity, One of these analogues has shown excellent anticancer activity (Mortimer, C. G.; Wells, G.; Crochard, J. -P.; Stone, E. L; Bradshaw, T. D.; Stevens, M. F. G.; Westwell, A. D. *J. Med. Chem.* 2006, 49, 179). The structurally related benzoxazoles have also been reported to possess anticancer activity (Kumar, D.; Jacob, M. R.; Reynold, M. B.; Kerwin, S. M. *Bioorg. Med. Chem.* 2002, 10, 3994; Gong, B.; Hong, F.; Kohm, C.; Bonham, L.; Klein, P. *Bioorg. Med. Chem. Lett.* 2004, 14, 1455). During earlier studies in this laboratory PBDs have been linked to benzothiazole or benzoxazole through alkane chain, which have shown promising anticancer activity. (Kamal, A.; Reddy K. S.; Ahmed K. M. N.; Shetti R. V. C. R. N. C International Publication No WO 2008/099416 A2). However, in the present invention the PBD and benzothiazole or benzoxazole moieties have been linked through piperazine moiety with alkyl side arms, instead simple alkane chain spacers. By incorporation of a piperazine moiety in the spacer these new hybrids not only exhibit enhanced in vitro activity but also remarkable DNA binding affinity for a number of this type of hybrids as illustrated in Table 1 and 2.

References may be made to patent "WO/2008/099416" wherein Benzothiazole or benzoxazole linked Pyrrolo[2,1-c][1,4] benzodiazepine hybrid as anticancer agent has been reported. References may be made to patent "U.S. Pat. No. 6,979,684" wherein Pyrrolo[2,1-c][1,4] benzodiazepine and naphthalimide are linked through piperazine moiety. The linking of pharmacophore like napthalimide and piperazine to pyrroloberizodiazepine can not be considered similar to a pharmacophore like benzothiazole as each pharmacophore is known for certain biological property. In the present investigation the benzothiaole and piperazine subunits are considered to be a different heterocyclic moieties compared to the earlier reported pharmacophores like napthalimide. Therefore, this structural variation of benzothiazole with piperazine moiety has been utilized for DNA binding aspect. Keeping this in mind, these new conjugates have been designed and synthesized to further improve the anticancer activity including the DNA binding affinity. The anticancer activity may not depend on the DNA binding activity. The DNA binding activity is only a biophysical aspect, therefore comparison of this data has no significance for the biological profile of the compounds. The new molecules of the present investigation exhibit potential anticancer activity. Moreover, one of the potent conjugate 9f (IICT-302) of this series has been evaluated for its in vivo efficacy studies (in scid male mice) against MCF-7 (breast cancer) and PC-3 (prostate cancer) xenografts by using adriamycin as a positive control. The in vivo efficacy study of 9f has exhibited less toxicity, good survival data and good RTV then control adriamycin indicating the potential use of these molecules in treating cancer.

OBJECTIVES OF THE INVENTION

The main objective of the present invention is to provide Pyrrolo[2,1-c][1,4]benzodiazepine-benzothiazole or benzoxazole conjugates linked through piperazine moiety useful as antitumour agents. Yet another object of the present invention is to provide a process for the preparation of Pyrrolo [2,1-c][1,4]benzodiazepine-benzothiazole or benzoxazole conjugates linked through piperazine moiety.

SUMMARY OF THE INVENTION

Accordingly, present invention provides Pyrrolo[2,1-c][1,4] benzodiazepine-benzothiazole or benzoxazole conjugates linked through piperzine moiety of general formula 9,

GENERAL FORMULA 9

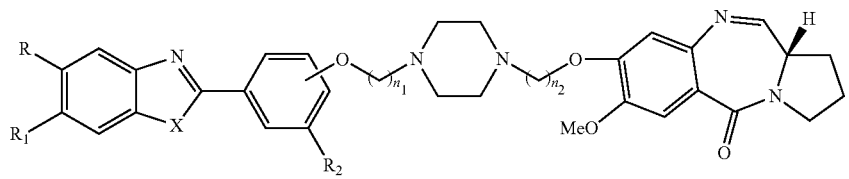

Wherein: R, $R_1$,=H, F, $OCF_3$, $CF_3$, Cl or OMe;
$R_2$=$OCH_3$ or H;
$n_1$, $n_2$=3 or 4;
X=S or O.

In an embodiment of the present invention, representative compounds of general formula 9 are:

7-Methoxy-8-[3-(4-{4-[3(1,3-benzothiazol-2-yl)-phenoxy]propyl}piperazin-1-yl) propyl]oxy-(11aS) -1,2,3,11a-tetrahydro-5H-pyrrolo[2,1-c][1,4]benzodiazepin-5-one (9a);

7-Methoxy-8-[3-(4-{4-[3(1,3-benzothiazol-2-yl)-2-methoxyphenoxy]propyl}piperazin-1-yl)propyl]oxy-(11aS)-1,2,3,11a-tetrahydro-5H-pyrrolo[2,1-c][1,4]benzodiazepin-5-one (9b);

7-Methoxy-8-[3-(4-{4-[3(6-flouro-1,3-benzothiazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9c);

7-Methoxy-8-[3-(4-{3- [3(1,3-benzothiazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9d);

7-Methoxy-8-[4-(4-{4-[4(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9e);

7-Methoxy-8-[4-(4-{4-[4(1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9f);

7-Methoxy-8-[4-(4-{4-[4(6-fluoro-1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9g);

7-Methoxy-8-[4-(4-{4-[3(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9h).

7-Methoxy-8-[3-(4-{4-[3(1,3-benzoxazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9i);

7-Methoxy-8-[3-(4-{4-[3(1,3-benzoxazol-2-yl)-2-methoxyphenoxy]propyl}piperazin-1-yl)propyl]oxy-(11aS)-1,2,3,11a-tetrahydro-5H-pyrrolo[2,1-c][1,4]benzodiazepin-5-one (9j);

7-Methoxy-8-[3-(4-{3-[3(1,3-benzoxazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9k);

7-Methoxy-8-[4-(4-{4-[4(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9l);

7-Methoxy-8-[4-(4-{4-[4(1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9m);

7-Methoxy-8-[4-(4-{4-[3(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one(9n);

7-Methoxy-8-[4-(4-{3-[4(,3-benzothiazol-2-yl)-4-methoxyphenoxy]butyl}piperazin-1-yl)butyl]oxy-(11aS)-1,2,3,11a-tetrahydro-5H-pyrrolo[2,1-c][1,4]benzodiazepin-5-one (9o);

7-Methoxy-8-[4-(4-{4-[4(6-trifluoromethyl-1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9p);

7-Methoxy-8-[4-(4-{4-[4(6-trifluoromethoxy-1,3-benzothiazol-2-yl)-2-methoxyphenoxy]butyl}piperazin-1-yl)butyl]oxy-(11aS)-1,2,3,11a-tetrahydro-5H- pyrrolo[2,1-c][1,4]benzodiazepin-5-one (9q);

7-Methoxy-8-[4-(4-{4-[4(6-methoxy-1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9r);

7-Methoxy-8-[4-(4-{4-[4(5-fluoro-1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9s);

7-Methoxy-8-[4-(4-{4-[4(6-chloro-1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9t);

7-Methoxy-8-[4-(4-{4-[4(5-fluoro-1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9u);

7-Methoxy-8-[4-(4-{4-[4(6-methoxy-1,3-benzoxazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9v);

7-Methoxy-8-[4-(4-{4-[4(6-trifluoromethoxy-1,3-benzoxazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9w);

7-Methoxy-8-[4-(4-{4-[4(6-fluoro-1,3-benzoxazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9x);

7-Methoxy-8-[4-(4-{4-[4(5-fluoro-1,3-benzoxazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9y);

7-Methoxy-8-[4-(4-{4-[4(6-chloro-1,3-benzoxazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9z).

In yet another embodiment of the present invention, structural formula of the representative compounds of general formula 9 are:

(9a)

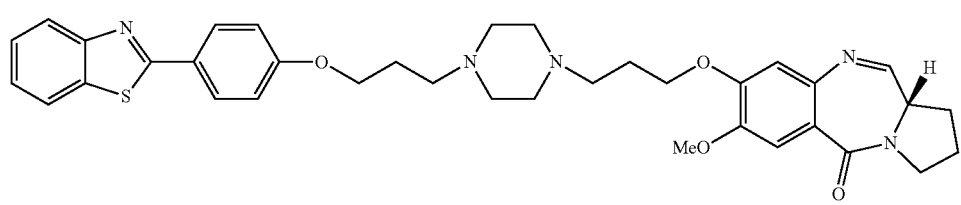

-continued
(9b)
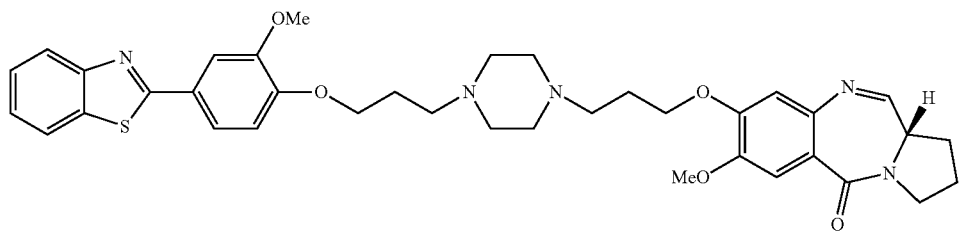
(9c)
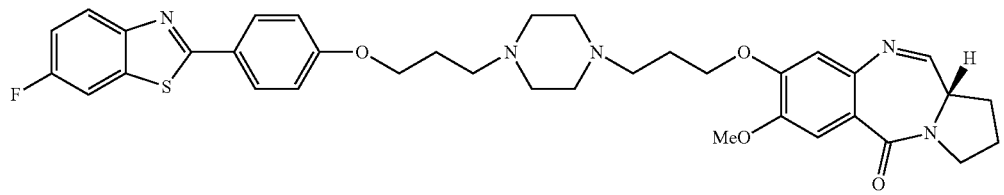
(9d)
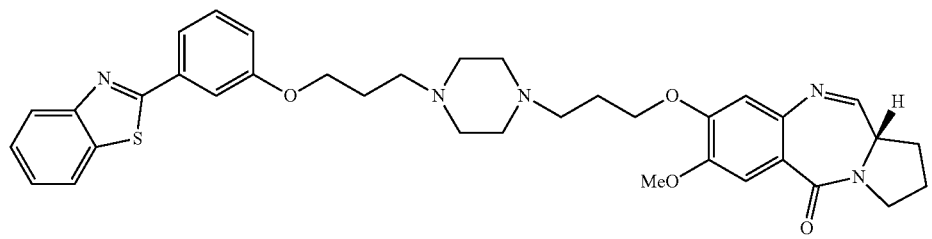
(9e)
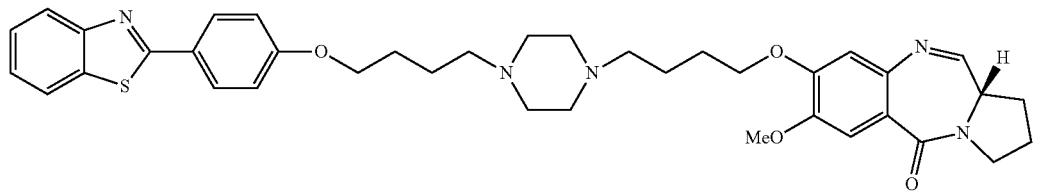
(9f)
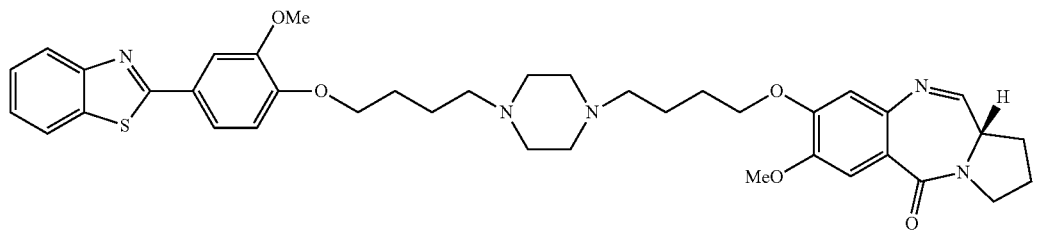
(9g)
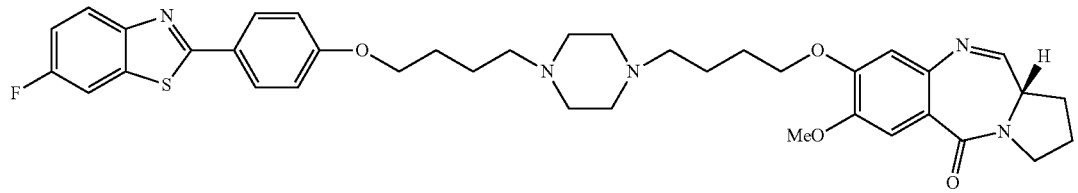
(9h)
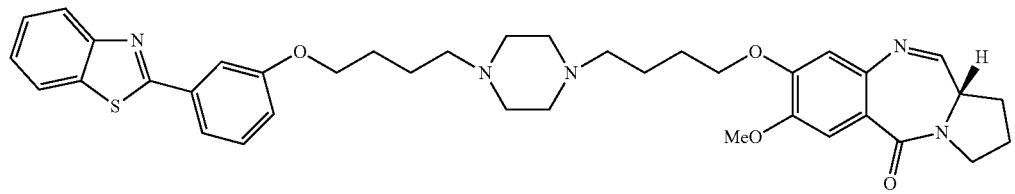

-continued
(9i)
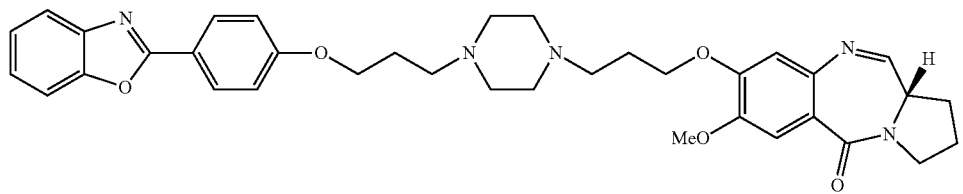
(9j)
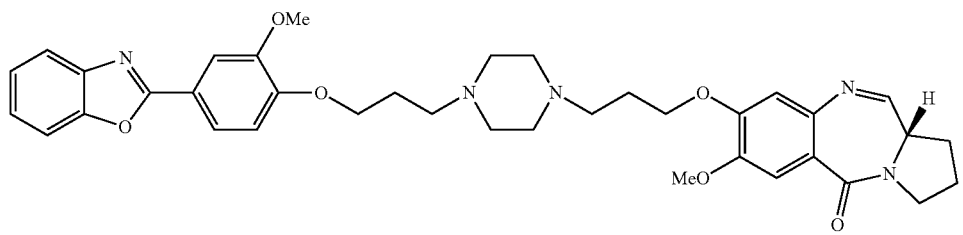
(9k)
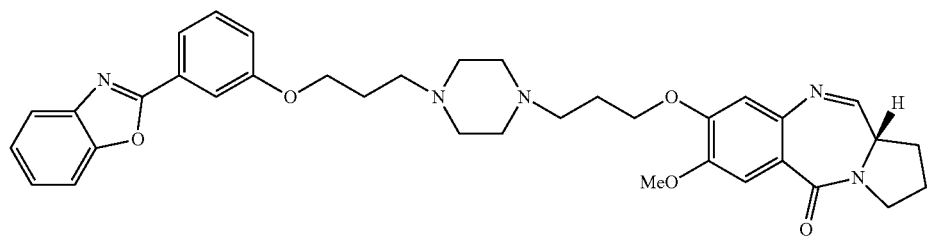
(9l)
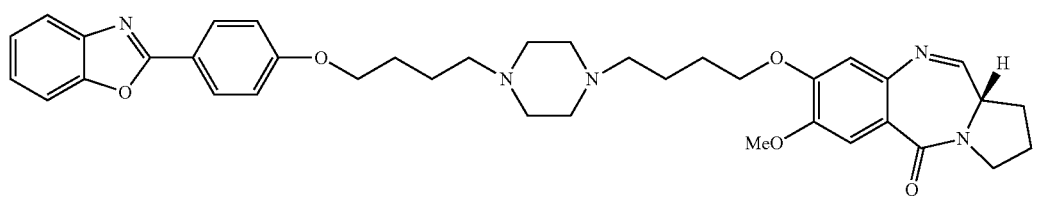
(9m)
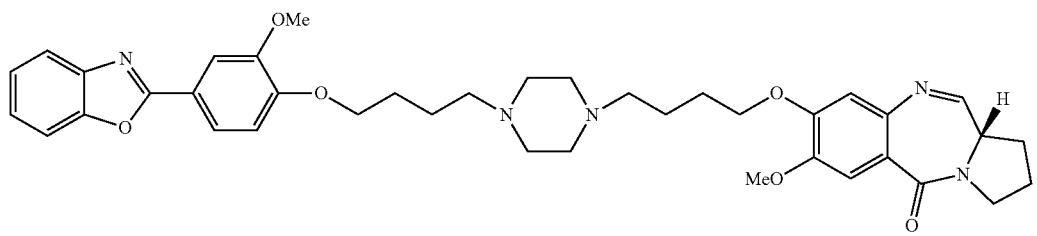
(9n)
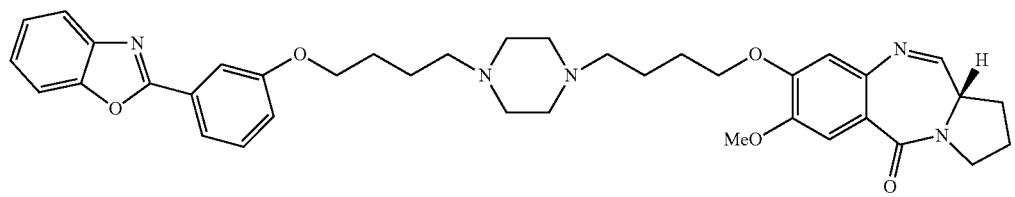
(9o)
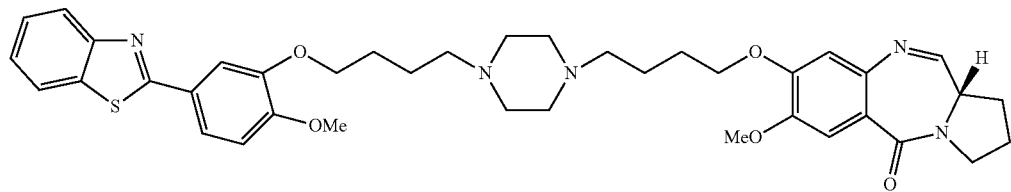

-continued
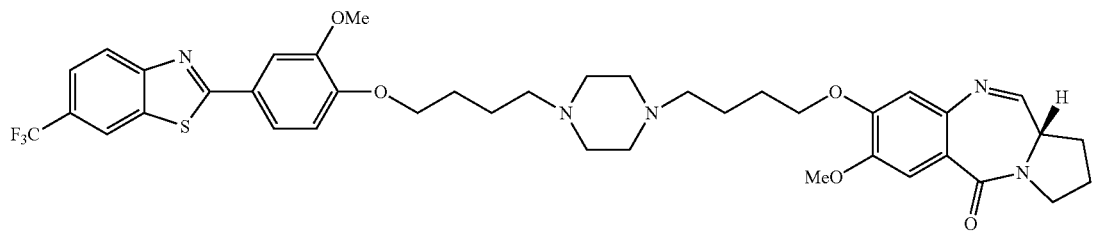
(9p)
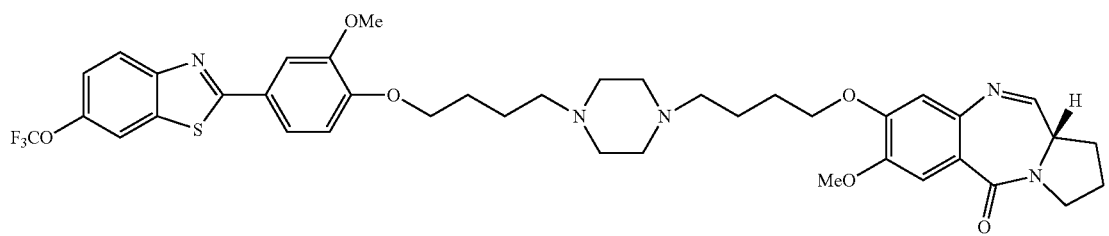
(9q)
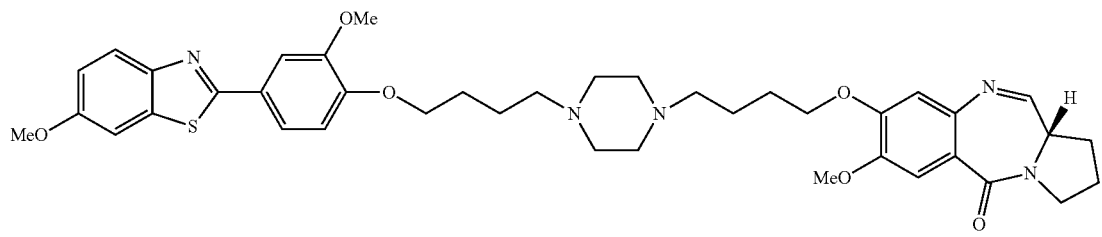
(9r)
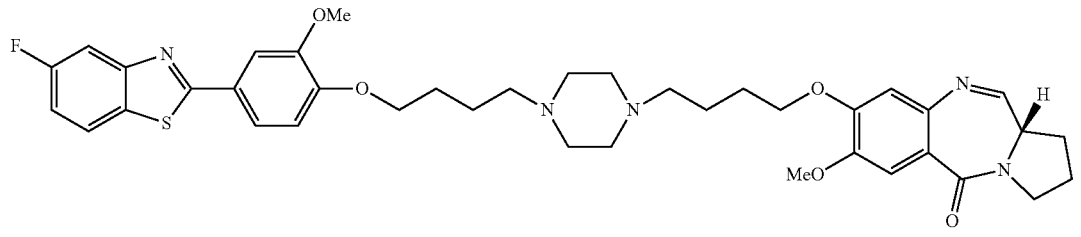
(9s)
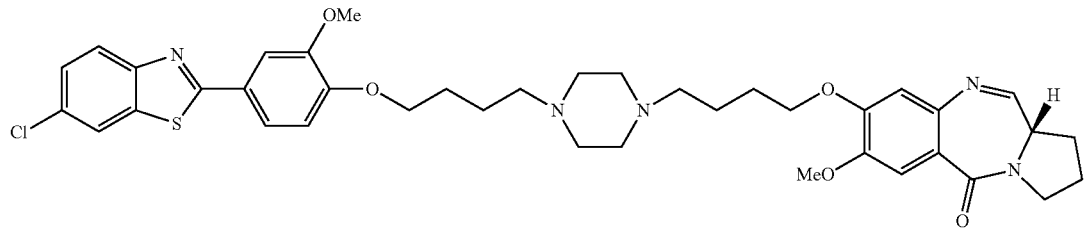
(9t)
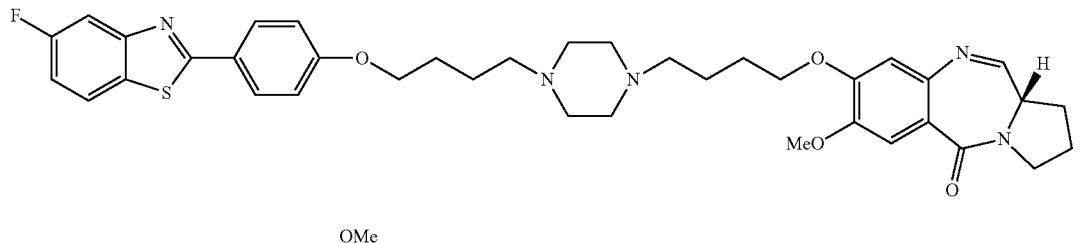
(9u)
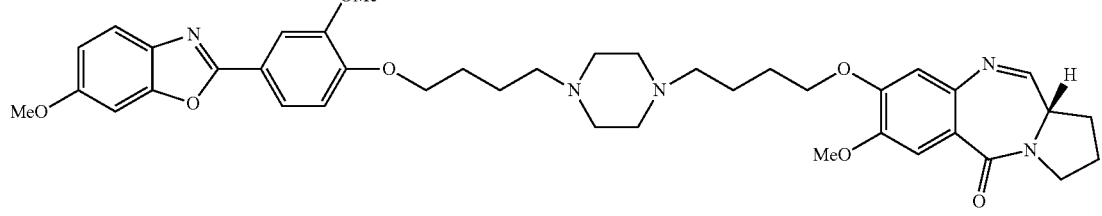
(9v)

-continued (9w)
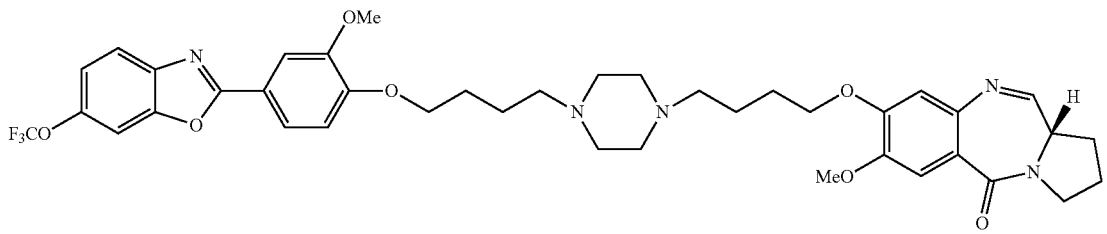

(9x)
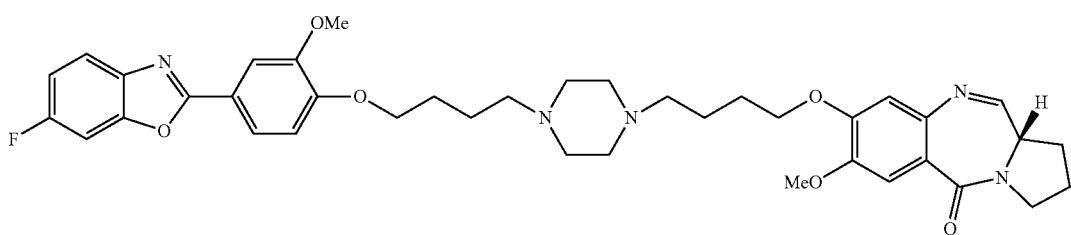

(9y)
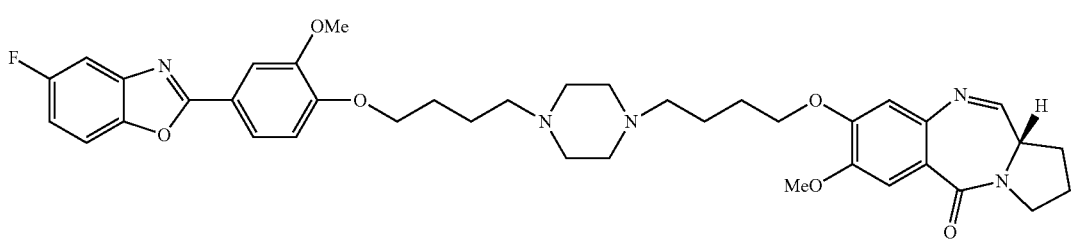

(9z)
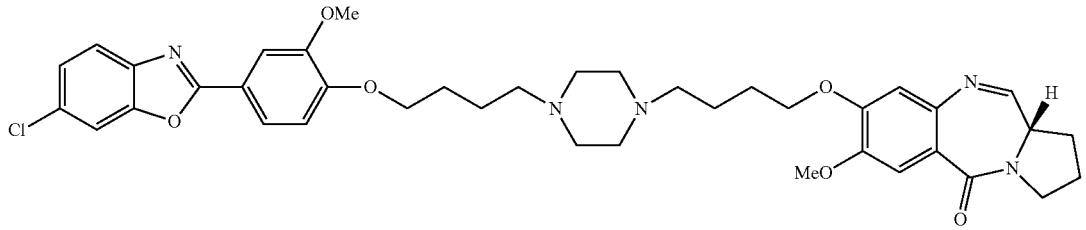

In yet another embodiment of the present invention, said compounds are useful as anticancer agent. In yet another embodiment of the present invention, said compounds exhibiting in-vitro anticancer activity against human cancer cell lines derived from nine cancer types of leukemia cancer cell line, non-small-cell lung cancer cell line, colon cancer cell line, CNS cancer cell line, melanoma cancer cell line, ovarian cancer cell line, prostate cancer cell line, and breast cancer cell line.

In yet another embodiment of the present invention, concentration of the compound 9a-l used for in-vitro activity against breast (MCF-7) cancer cell line for $GI_{50}$ and $LC_{50}$ are in the range of <0.01 to 0.14 μm and <0.01 to 2.6 μm respectively at an exposure period of at least 48 hrs.

In yet another embodiment of the present invention, concentration of the compound 9a-l used for in-vitro activity against colon (Colo205) cancer cell line for $GI_{50}$ and $LC_{50}$ are in the range of <0.01 to 0.17 μm and >$10^2$ μm respectively at an exposure period of at least 48 hrs.

In yet another embodiment of the present invention, concentration of the compound 9a-l used for in-vitro activity against non small cell lung (A549) cancer cell line for $GI_{50}$ and LC 50 are in the range of <0.01 to 0.13 μm and 30 to >$10^2$ μm respectively at an exposure period of at least 48 hrs.

In yet another embodiment of the present invention, concentration of the compound 9a-l used for in-vitro activity against non small cell lung (HOP 62) cancer cell line for $GI_{50}$ and LC 50 are in the range of <0.01 to 0.16 μm and 2.3 to >$10^2$ μm respectively at an exposure period of at least 48 hrs.

In yet another embodiment of the present invention, concentration of the compound 9a-l used for in-vitro activity against ovarian (A 2780) cancer cell line for $GI_{50}$ and LC 50 are in the range of <0.01 to 0.147 μm and 0.089 to 23 μm respectively at an exposure period of at least 48 hrs.

In yet another embodiment of the present invention, concentration of the compound 9a-l used for in-vitro activity against prostate (Pc 3) cancer cell line for $GI_{50}$ and LC 50 are in the range of <0.01 to 0.16 μm and 0.23 to 31 μm respectively at an exposure period of at least 48 hrs.

In yet another embodiment of the present invention, concentration of the compound 9a-l used for in-vitro activity against cervix (SiHa) cancer cell line for $GI_{50}$ and LC 50 are in the range of <0.01 to 0.168 μm and 0.311 to 28.5 μm respectively at an exposure period of at least 48 hrs.

In yet another embodiment of the present invention, concentration of the compound 9a-l used for in-vitro activity against oral (KB) cancer cell line for $GI_{50}$ and LC 50 are in the range of <0.01 to 0.16 μm and 0.18 to >$10^2$ μm respectively at an exposure period of at least 48 hrs.

In an embodiment, a process for the preparation of pyrrolo [2,1-c][1,4]benzodiazepine-benzothiazole or benzoxazole conjugates linked through piperzine of general formula 9 and the said process comprising the steps of:

i. etherifying compound of formula 1 with dibromo alkanes in acetone reflux at 80° C. for 12 h to obtain compound of formula 2a, b;

1

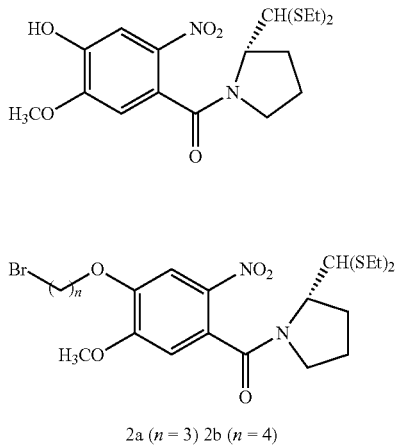

2a (n = 3) 2b (n = 4)

ii. coupling compound of formula 2a,b as obtained in step (i) with N-Boc piperazine in acetone reflux at 80° C. for 24 h to produce 3a,b;

3a-b

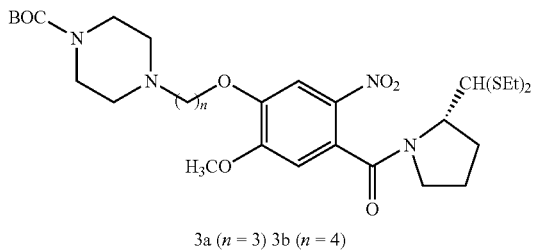

3a (n = 3) 3b (n = 4)

iii. deprotecting compound of formula 3a,b by using Triflubroacetic acid (TFA) at 27° C. for 12 h to obtain compounds of formula 4a-b;

4a-b

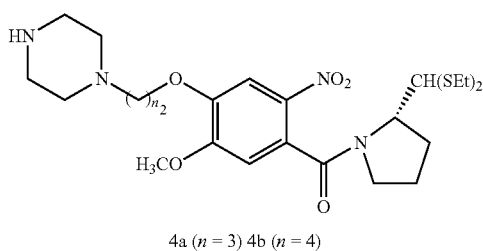

4a (n = 3) 4b (n = 4)

iv. condensing substituted 2-aminothiophenol or 2-aminophenols with 4-hydroxy benzaldehyde, 3-hydroxy benzaldehyde, vanilline, isovanillline or benzylated protected berizaldehydes, oxidation followed by debenzylation with palladium on charcoal to obtain to obtain precursors 5a-s;

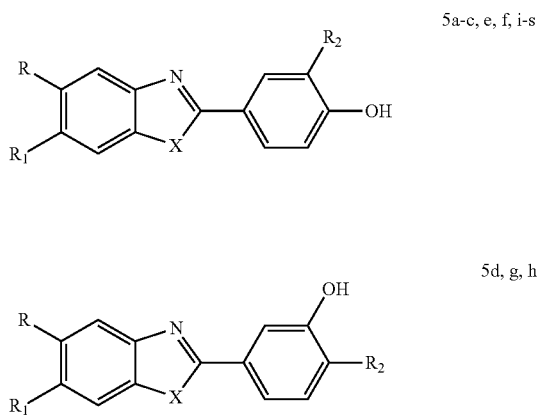

v. etherifying precursors as obtained in step (iv) with dibromoalkanes in presence of $K_2CO_3$ in acetone at 80° C. for 12 h to obtain benzothiazole/benzoxazole precursors of formula 6a-z;

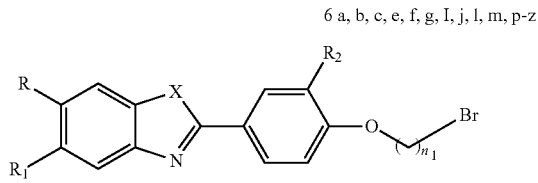

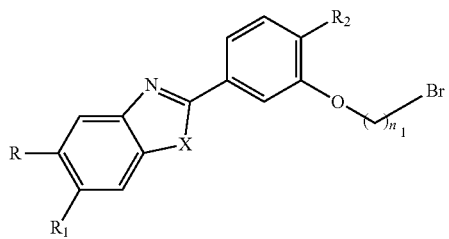

vi. reacting a compound of formula 4a-b as obtained in step (iii) with benzothiazole or benzoxazote derivative selected from the compound of formula 6a-z as obtained in step (v) in the presence of $K_2CO_3$, in acetone solvent, under refluxing temperature in the range of 70-75° C. to obtain the resultant nitro compound of formula 7a-z;

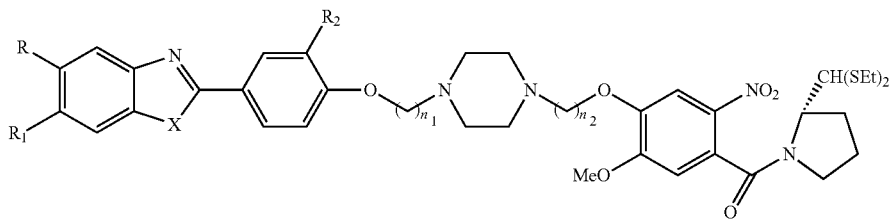

7a, b, c, e, f, g, i, j, l, m, p-z

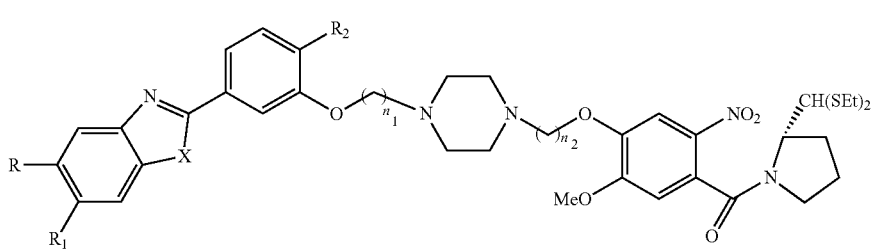

7d, h, k, n, o vii. reducing the above said nitro compound of formula 7a-z as obtained in step (vi) with SnCl$_2$.2H$_2$O in methanol solvent, under reflux temperature in the range of 80-85° C. and isolating the corresponding amino compound of formula 8a-z;

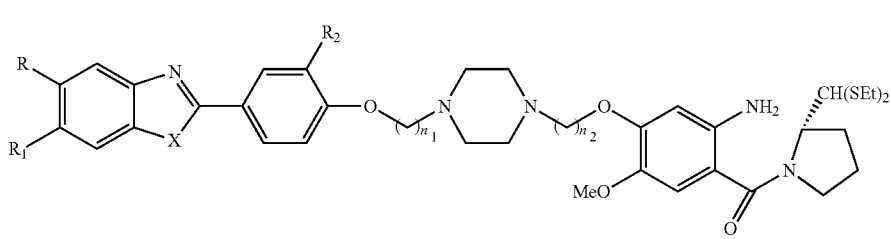

8a, b, c, e, f, g, i, j, l, m, p-z

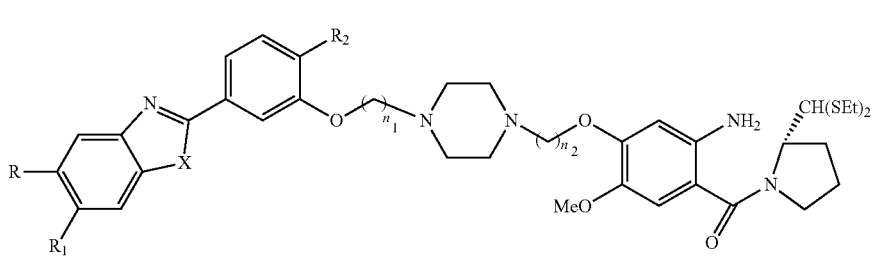

8d, h, k, n, o viii. reacting the above said amino compound of formula 8 as obtained in step (vii) with a deprotecting agent etanethiol/BF$_3$.OEt$_2$ by known method to obtain the desired compound of formula 9.

In an embodiment, a process for the preparation of pyrrolo[2,1-c][1,4]benzodiazepine-benzothiazole or benzoxazole conjugates linked through piperzine of general formula 9 and the said process comprising the steps of:

a. reacting a compound of formula 4a-b

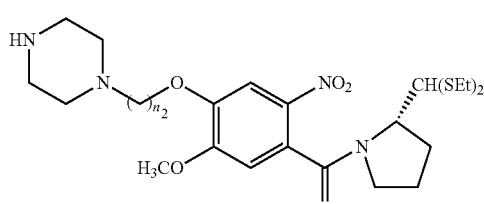

4a-b 4a (n = 3) 4b (n = 4)

with benzothiazole or benzoxazole derivative selected from the compound of formula 6a-z

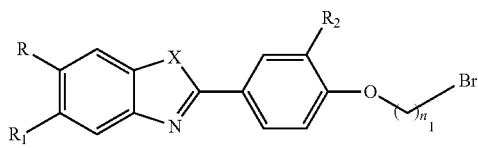

6 a, b, c, e, f, g, I, j, l, m, p-z

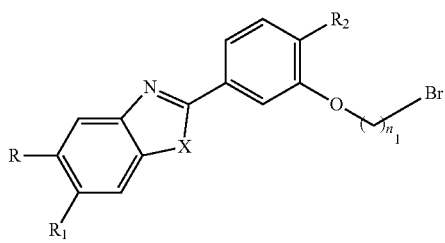

6 d, h, k, n, o in the presence of K$_2$CO$_3$, in acetone solvent, under refluxing temperature in the range of 70-75° C. to obtain the resultant nitro compound of formula 7a-z;

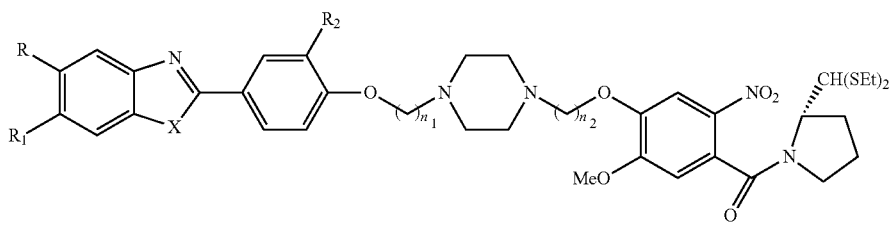

7a, b, c, e, f, g, i, j, l, m, p-z

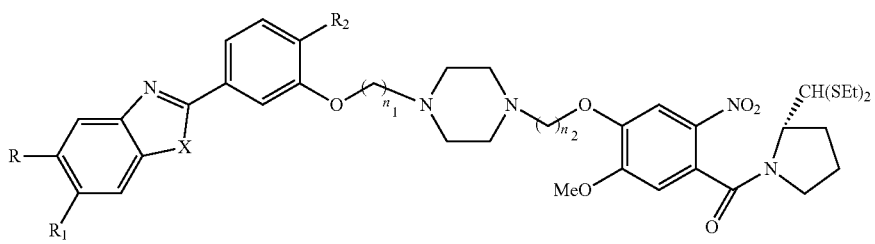

7d, h, k, n, o b. reducing the above said nitro compound of formula 7a-z as obtained in step (a) with SnCl$_2$.2H$_2$O in methanol solvent, under reflux temperature in the range of 80-85° C. and isolating the corresponding amino compound of formula 8a-z;

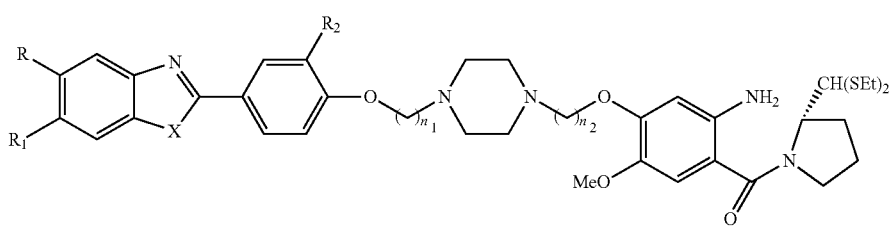

8a, b, c, e, f, g, i, j, l, m, p-z

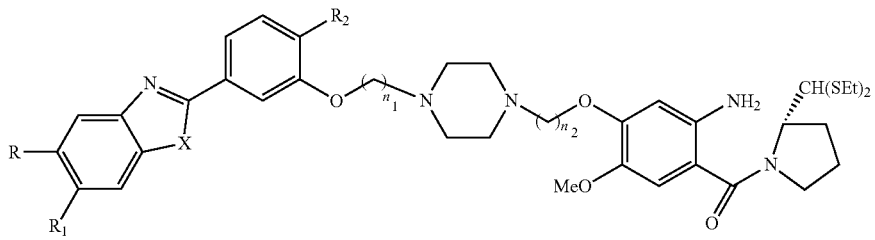

8d, h, k, n, o c. reacting the above said amino compound of formula 8 as obtained in step (b) with a deprotecting agent etanethiol/ BF$_3$.OEt$_2$ by known method to obtain the desired compound of formula 9.

BRIEF DESCRIPTION OF THE DRAWINGS

Scheme 1 shows the synthesis of benzothiozole/benzoxazole-PBD conjugates (9a-c; 9e-g; 9i-j; 9l-m and 9p-z) linked through Piperazine moiety. Compounds 4a or 4b has been coupled to 6a-c; 6e-g; 6i-j; 6l-m and 6p-z to give corresponding nitrothioacetals 7a-c; 7e-g; 7i-j; 7l-m and 7p-z respectively. These coupled nitrothioacetal intermediates reduced with SnCl$_2$.2H$_2$O in methanol affords amino thioacetal precursors 8a-c; 8e-g; 8i-j; 8l-m and 8p-z. This on deportation by HgCl$_2$/CaCO$_3$ affords desire PBD conjugates 9a-c; 9e-g; 9i-j; 9l-m and 9p-z.

Scheme 2 shows the synthesis of benzothiozole/benzoxazole-PBD conjugates (9d, 9h, 9k, 9n or 9o) linked through Piperazine moiety. Compounds 4a or 4b has been coupled to 6d, 6h, 6k, 6n or 6o to give corresponding nitrothioacetals 7d, 7h, 7k and 7n,o respectively. These coupled nitrothioacetal intermediates reduced with SnCl$_2$.2H$_2$O in methanol affords amino thioacetal precursors 8d, 8h, 8k, 8n or 8o. This on deportation by HgCl$_2$/CaCO$_3$ affords desire PBD conjugates 9d, 9h, 9k and 9n or 9o.

DETAILED DESCRIPTION OF THE INVENTION

Figure 1:
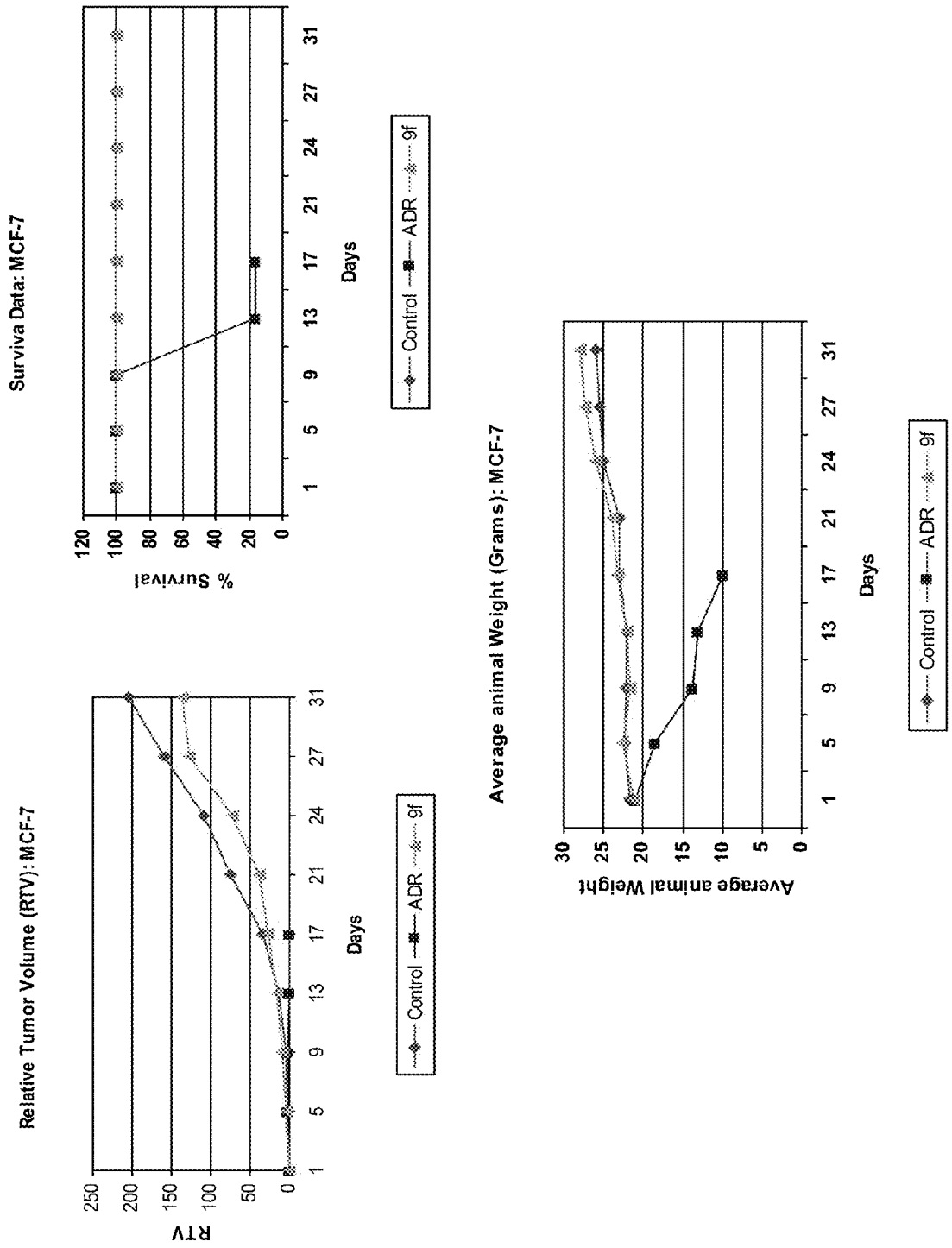
FIG. 1 represent some compounds of formula 1, 2a-b, 3a-b and 5a-s.
Figure 2:
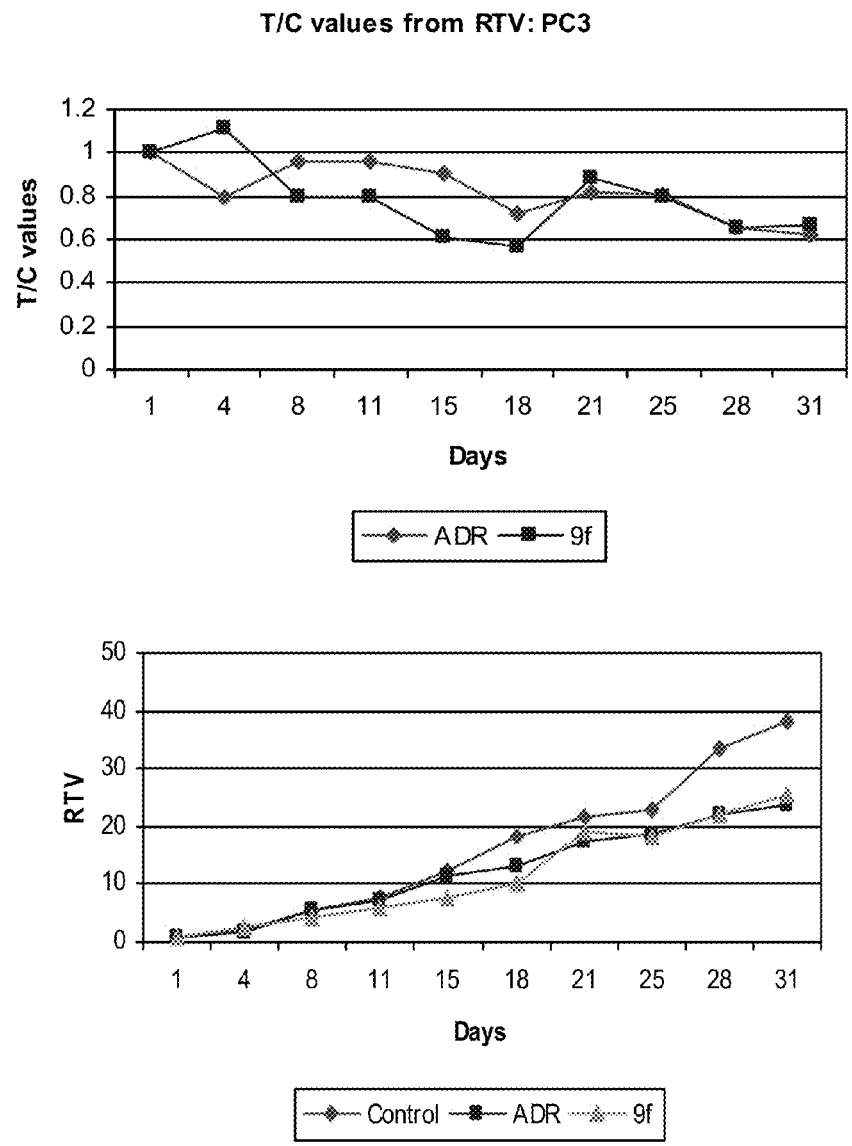
FIG. 2 represents in vivo efficacy study of compound 9f on xenograft MCF-7.
Figure 3:
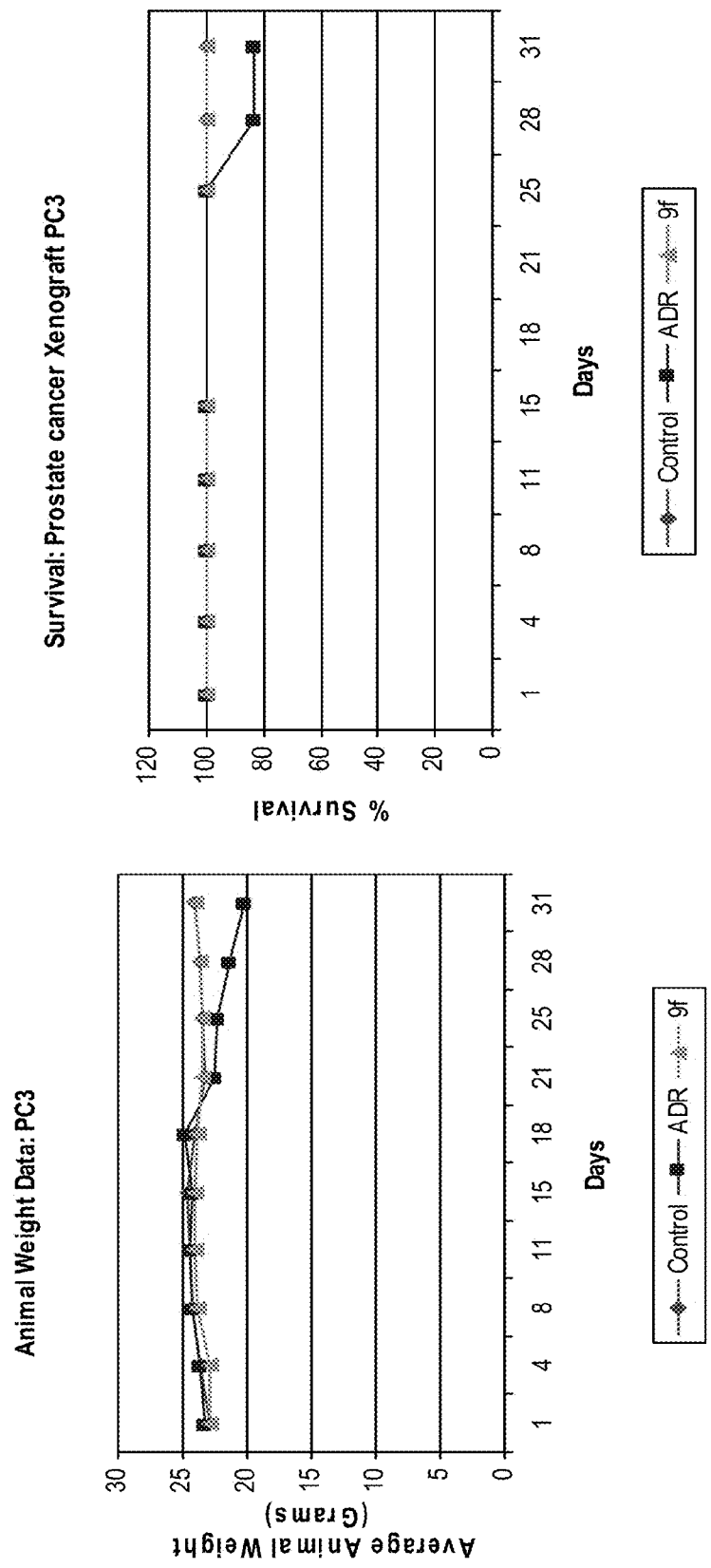
FIG. 3 represents in vivo efficacy study of compound 9f on xenograft PC3.

The precursors (2S)-N-[4-(hydroxy-5-methoxy-2-nitrobenzoyl]pyrrplidine-2-carboxaldehyde diethyl thioacetal of formula 1 (Thurston, D. E.; Murthy, V. S.; Langley, D. R.; Jones, G. B. *Synthesis*. 1990, 81), (2S)-[N-{4-(3-(piperzin-1-yl)alkyl)-5-methoxy-2-nitro benzoyl] pyrrolidine-2-carboxaldehyde. diethylthioacetal of formula 4a,b (Ahmed Kamal, M. Naseer A. Khan, K. Srinivasa Reddy, S. Kaleem Bio-Med Chem Lett 2007, 17, 5345-5348) and the 4/3-(1,3benzothiazol-2-yl-5/6-alkyl/alkoxy/halo)phenol/4/3-(1,3-benzothiazol-2-yl-5/6-alkyl/alkoxy/halo)-2-methoxyphenol of formula 5a-d and 5h-5n have been prepared by literature methods (Ben-Allum, A.; Bakkas, S.; Soufiaoui, M. *Tetrahedron Lett*. 1997, 38, 6395; Wells, G.; Lowe, P. R.; Stevens, M. F. G. ARKIVOC 2000, 1, 779). The benzoxazole precursors 5e-g and 5o-s have been prepared by condensation of 2-aminophenols with benzylated protected benzaldehydes, oxidation followed by debenzylation with palladium on charcoal (Centore, R.; Panunzi, B.; Roviello, A.; Sirigu, A.; Villano, P. *J. Polym. Sci. Part A: Polym. Chem*. 1996, 34, 3203). The benzothiazole/benzoxazole precursors (formula 6a-z) have been prepared by etherfication reaction between compounds 5a-s and dibromoalkanes in presence of K$_2$CO$_3$ in acetone at 80° C. for 12 h.

Synthesis of compound 1 has been carried out by employing commercially available vanillin. Oxidation of vanillin, followed by benzylation and nitration provides 4-benzyloxy-5-methoxy-2-nitrobenzoic acid. This has been further coupled to L-Proline methyl ester, which upon reduction with DIBAL-H produces the corresponding aldehyde. The aldehyde group of this product has been protected with EtSH/ TMSCl and upon debenzylation affords (2S)-N-[4-hydroxy-5-methoxy-2-nitrobenzoyl]pyrolidine-2-carboxaldehyde diethyl thioacetal (formula 1) by employing literate methods, which upon etherification by dibromo alkanes affords 2a,b in acetone reflux (80° C.) for 12 h. These compounds have been coupled to N-Boc piperazine in acetone reflux (80° C) for 24 h to produce 3a,b. The compounds 3a,b has been deprotected by using TFA affords compounds 4a,b at 27° C. for 12 h.

The precursors 5a-d and 5h-5n have been prepared by the condensation of substituted 2-aminothiophenol with 4-hydroxy benzaldehyde, 3-hydroxy benzaldehyde, vanillin or isovanillline. The benzoxazole precursors 5e-g and 5o-s have been prepared by condensation of 2-aminophenols with benzylated protected benzaldehydes, oxidation followed by debenzylation with palladium on charcoal. The benzothiazole/benzoxazole precursors (formula 6a-z) have been prepared by etherfication reaction between compounds 5a-s and dibromoalkanes in presence of K$_2$CO$_3$ in acetone at 80° C. for 12 h.

These pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. Process steps are:

1) The ether linkage at C-8 position of DC-81 intermediates with benzothiazole and benzoxazole moieties.
2) Refluxing the reaction mixtures for 48 h.
3) Synthesis of C-8 linked PBD antitumour antibiotic hybrid imines.
4) Purification by column chromatography using different solvents like ethyl acetate, hexane, chloroform and methanol.

TABLE 1

Representative formulas of hydroxybenzothiazloe/benzoxazole intermediates.

| S. No | Comp | R | R$_1$ | R$_2$ | X |
|---|---|---|---|---|---|
| 1. | 5a | H | H | H | S |
| 2. | 5b | H | H | OMe | S |

TABLE 1-continued

Representative formulas of hydroxybenzothiazloe/benzoxazole intermediates.

| S. No | Comp | R | $R_1$ | $R_2$ | X |
|---|---|---|---|---|---|
| 3. | 5c | H | F | H | S |
| 4. | 5d | H | H | H | S |
| 5. | 5e | H | H | H | O |
| 6. | 5f | H | H | OMe | O |
| 7. | 5g | H | H | H | O |
| 8. | 5h | H | H | OMe | S |
| 9. | 5i | H | $CF_3$ | OMe | S |
| 10. | 5j | H | $OCF_3$ | OMe | S |
| 11. | 5k | H | OMe | OMe | S |
| 12. | 5l | F | H | OMe | S |
| 13. | 5m | H | Cl | OMe | S |
| 14. | 5n | F | H | H | S |
| 15. | 5o | H | OMe | OMe | O |
| 16. | 5p | H | $OCF_3$ | OMe | O |
| 17. | 5q | H | F | OMe | O |
| 18. | 5r | F | F | OMe | O |
| 19 | 5s | H | Cl | OMe | O |

TABLE 2

Representative formulas of benzothiazloe/benzoxazole intermediates.

| S. No | Comp | Comp | Comp | R | $R_1$ | $R_2$ | X | $n_1$ |
|---|---|---|---|---|---|---|---|---|
| 1. | 6a | 7a | 8a | H | H | H | S | 3 |
| 2. | 6b | 7b | 8b | H | H | OMe | S | 3 |
| 3. | 6c | 7c | 8c | H | F | H | S | 3 |
| 4. | 6d | 7d | 8d | H | H | H | S | 3 |
| 5. | 6e | 7e | 8e | H | H | H | S | 4 |
| 6. | 6f | 7f | 8f | H | H | OMe | S | 4 |
| 7. | 6g | 7g | 8g | H | F | H | S | 4 |
| 8. | 6h | 7h | 8h | H | H | H | S | 4 |
| 9. | 6i | 7i | 8i | H | H | H | O | 3 |
| 10. | 6j | 7j | 8j | H | H | OMe | O | 3 |
| 11. | 6k | 7k | 8k | H | H | H | O | 3 |
| 12. | 6l | 7l | 8l | H | H | H | O | 4 |
| 13. | 6m | 7m | 8m | H | H | OMe | O | 4 |
| 14. | 6n | 7n | 8n | H | H | H | O | 4 |
| 15 | 6o | 7o | 8o | H | H | OMe | S | 4 |
| 16 | 6p | 7p | 8p | H | $CF_3$ | OMe | S | 4 |
| 17 | 6q | 7q | 8q | H | $OCF_3$ | OMe | S | 4 |
| 18 | 6r | 7r | 8r | H | OMe | OMe | S | 4 |
| 19 | 6s | 7s | 8s | F | H | OMe | S | 4 |
| 20 | 6t | 7t | 8t | H | Cl | OMe | S | 4 |
| 21 | 6u | 7u | 8u | F | H | H | S | 4 |
| 22 | 6v | 7v | 8v | H | OMe | OMe | O | 4 |
| 23 | 6w | 7w | 8w | H | $OCF_3$ | OMe | O | 4 |
| 24 | 6x | 7x | 8x | H | F | OMe | O | 4 |
| 25 | 6y | 7y | 8y | F | F | OMe | O | 4 |
| 26 | 6z | 7z | 8z | H | Cl | OMe | O | 4 |

Comparative Data

TABLE 3

Comparative data of DNA binding affinity of benzothiazole and benzoxazole linked PBD hybrids with piperizine and with out piperizine.

| PBD hybrids (with out piperizine) | $(\Delta T_m (°C.))^a$ after incubation at 37° C. for 0 h | $(\Delta T_m (°C.))^a$ after incubation at 37° C. for 18 h | PBD hybrids (with piperizine) | $(\Delta T_m (°C.))^a$ after incubation at 37° C. for 0 h | $(\Delta T_m (°C.))^a$ after incubation at 37° C. for 18 h |
|---|---|---|---|---|---|
| 20a | 0.5 | 0.5 | 9a | 10.2 | 10.8 |
| 20b | 0.5 | 0.5 | 9b | 12.1 | 12.7 |
| 20c | 4.1 | 4.3 | 9c | 10.3 | 10.7 |
| 20d | 6.2 | 6.3 | 9d | 11.2 | 11.5 |
| 23b | 0.5 | 0.5 | 9e | 12.2 | 12.6 |
| 26 | 2.1 | 4.2 | 9f | 15.5 | 15.9 |
| 30a | 4.1 | 4.3 | 9g | 12.3 | 12.6 |
| 30b | 4.2 | 4.3 | 9h | 11.9 | 12.3 |
| | | | 9i | 9.5 | 9.7 |
| | | | 9j | 10.1 | 10.3 |
| | | | 9k | 9.7 | 10.2 |
| | | | 9l | 11.5 | 11.8 |
| | | | 9m | 12.1 | 12.5 |
| | | | 9n | 10.3 | 10.6 |
| | | | DC-81 | 0.3 | 0.7 |

[a] For CT-DNA alone at pH 7.00 ± 0.01, $T_m$ = 69.1° C. ± 0.01 (mean value from 10 separate determinations), all $\Delta T_m$ values are ±0.1-0.2° C.
[b] For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

TABLE 4

Comparative in vitro cytotoxicity data of benzothiazole and benzoxazle linked PBD hybrids with piperizine and with out piperizine in selected human cancer cell lines ($GI_{50}$ values[a] in μM concentration)

| hybrides with out piperazine | MCF 7[b] | IGROV1[c] | Colo 205[d] | PC 3[e] | Hybrides with piperazine | MCF 7[b] | A 2780[c] | Colo 205[d] | PC 3[e] |
|---|---|---|---|---|---|---|---|---|---|
| 20a | 0.32 | 2.42 | 0.34 | 0.29 | 9a | <0.01 | 0.108 | 0.1 | 0.12 |
| 20b | 0.40 | 3.06 | 0.69 | 0.41 | 9b | <0.01 | <0.01 | 0.09 | <0.01 |
| 20c | 0.33 | 2.69 | 0.38 | 0.23 | 9c | <0.01 | 0.116 | 0.13 | 0.11 |

TABLE 4-continued

Comparative in vitro cytotoxicity data of benzothiazole and benzoxazle linked PBD hybrids with piperizine and with out piperizine in selected human cancer cell lines ($GI_{50}$ values$^a$ in μM concentration)

| hybrides with out piperazine | MCF 7[b] | IGROV1[c] | Colo 205[d] | PC 3[e] | Hybrides with piperazine | MCF 7[b] | A 2780[c] | Colo 205[d] | PC 3[e] |
|---|---|---|---|---|---|---|---|---|---|
| 20d | 0.01 | 0.344 | 0.06 | 0.04 | 9d | 0.01 | 0.099 | 0.11 | <0.01 |
| | | | | | 9e | <0.01 | 0.097 | 0.12 | <0.01 |
| | | | | | 9f | <0.01 | <0.01 | <0.01 | <0.01 |
| | | | | | 9g | 0.14 | 0.147 | 0.1 | 0.16 |
| | | | | | 9h | 0.12 | 0.109 | 0.16 | 0.14 |
| | | | | | 9i | <0.01 | 0.08 | <0.01 | <0.01 |
| | | | | | 9j | <0.01 | <0.01 | 0.11 | <0.01 |
| | | | | | 9k | <0.01 | 0.086 | 0.17 | <0.01 |
| | | | | | 9l | <0.01 | 0.099 | <0.01 | <0.01 |
| | | | | | DC-81 | 0.16 | 0.13 | 0.10 | — |
| | | | | | ADR | <0.01 | 0.002 | 14.7 | <0.01 |

TABLE 5

Comparative in vitro cytotoxicity data of benzothiazole and benzoxazle linked PBD hybrids with piperizine and with out piperizine in selected human cancer cell lines ($GI_{50}$ values$^a$ in μM concentration)

| hybrides with out piperazine | SNB-19[f] | A 549[g] | HOP 62[g] | A498[h] | Hybrides with piperazine | SiHa[f] | A 549[g] | HOP 62[g] | KB[h] |
|---|---|---|---|---|---|---|---|---|---|
| 20a | 1.52 | 2.63 | 0.406 | 2.02 | 9a | 0.13 | 0.13 | 0.1 | 0.12 |
| 20b | 1.61 | 2.66 | 1.41 | 1.60 | 9b | <0.01 | 0.12 | <0.01 | <0.01 |
| 20c | 2.94 | 2.59 | 0.412 | 2.26 | 9c | 0.13 | <0.01 | 0.11 | 0.11 |
| 20d | 0.21 | 0.24 | 0.04 | 0.17 | 9d | 0.12 | <0.01 | <0.01 | 0.11 |
| | | | | | 9e | 0.107 | 0.105 | <0.01 | <0.01 |
| | | | | | 9f | <0.01 | <0.01 | <0.01 | <0.01 |
| | | | | | 9g | 0.168 | <0.01 | 0.16 | 0.16 |
| | | | | | 9h | 0.13 | 0.12 | 0.1 | 0.12 |
| | | | | | 9i | 0.117 | <0.01 | 0.11 | <0.01 |
| | | | | | 9j | <0.01 | <0.01 | <0.01 | <0.01 |
| | | | | | 9k | 0.13 | <0.01 | 0.01 | 0.11 |
| | | | | | 9l | 0.125 | <0.01 | 0.11 | 0.11 |
| | | | | | DC-81 | 0.16 | — | 0.11 | 0.17 |
| | | | | | ADR | 0.19 | 13 | <0.01 | 0.16 |

[a]50% Growth inhibition and the values are mean of three determinations,
[b]brest cancer,
[c]ovary cancer,
[d]colon cancer,
[e]prostate cancer,
[f]cervix cancer,
[g]lung cancer,
[h]oral cancer,
ADR, adriamycin

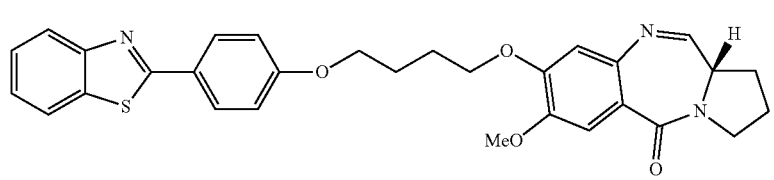

20a

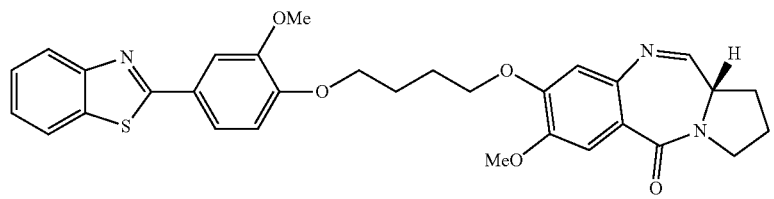

20b

-continued
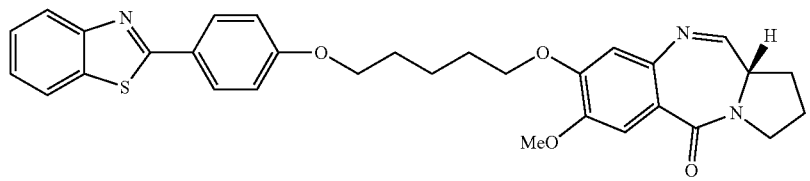
20c
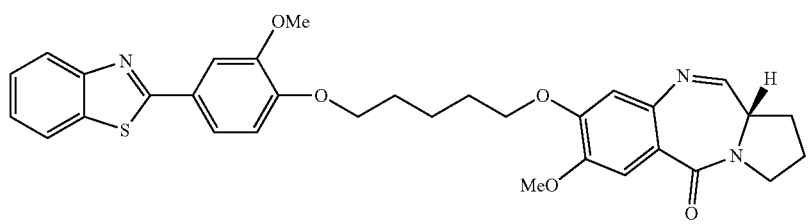
20d
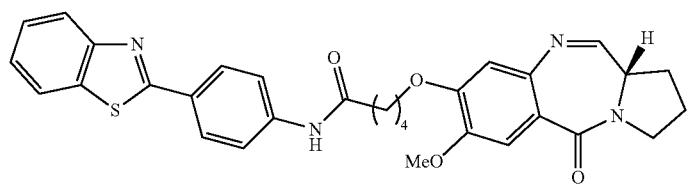
23b
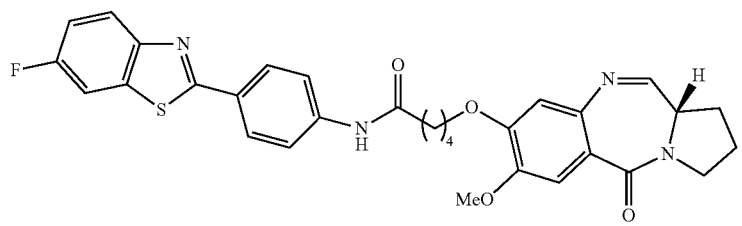
26
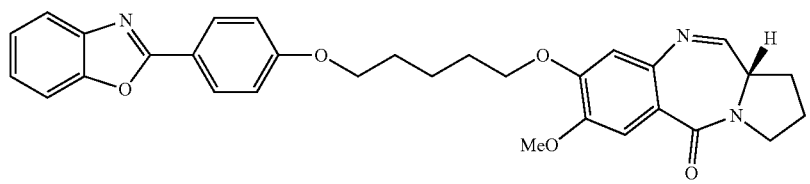
30a
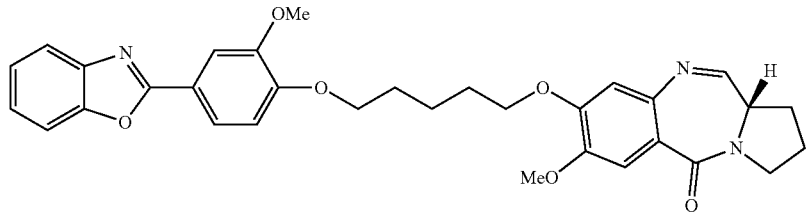
30b
TABLE 6
GI$_{50}$ values[a] (in μM) for compounds 9a-j in selected human cancer cell lines.
| Comp | MCF 7[b] | A 2780[c] | Colo 205[d] | PC 3[e] | SiHa[f] | A 549[g] | HOP 62[g] | KB[h] |
|------|---------|----------|-------------|---------|---------|----------|-----------|-------|
| 9a | <0.01 | 0.108 | 0.1 | 0.12 | 0.13 | 0.13 | 0.1 | 0.12 |
| 9b | <0.01 | <0.01 | 0.09 | <0.01 | <0.01 | 0.12 | <0.01 | <0.01 |
| 9c | <0.01 | 0.116 | 0.13 | 0.11 | 0.13 | <0.01 | 0.11 | 0.11 |
| 9e | <0.01 | 0.097 | 0.12 | <0.01 | 0.107 | 0.105 | <0.01 | <0.01 |
| 9f | <0.01 | <0.01 | <0.01 | <0.01 | <0.01 | <0.01 | <0.01 | <0.01 |
| 9g | 0.14 | 0.147 | 0.1 | 0.16 | 0.168 | <0.01 | 0.16 | 0.16 |
| 9i | <0.01 | 0.08 | <0.01 | <0.01 | 0.117 | <0.01 | 0.11 | <0.01 |
| 9j | <0.01 | <0.01 | 0.11 | <0.01 | <0.01 | <0.01 | <0.01 | <0.01 |
| 9k | <0.01 | 0.086 | 0.17 | <0.01 | 0.13 | <0.01 | 0.01 | 0.11 |

TABLE 6-continued

GI$_{50}$ values[a] (in μM) for compounds 9a-j in selected human cancer cell lines.

| Comp | MCF 7[b] | A 2780[c] | Colo 205[d] | PC 3[e] | SiHa[f] | A 549[g] | HOP 62[g] | KB[h] |
|---|---|---|---|---|---|---|---|---|
| 9l | <0.01 | 0.099 | <0.01 | <0.01 | 0.125 | <0.01 | 0.11 | 0.11 |
| DC-81 | 0.16 | 0.13 | 0.10 | — | 0.16 | — | 0.11 | 0.17 |
| ADR | <0.01 | 0.002 | 14.7 | <0.01 | 0.19 | 13 | <0.01 | 0.16 |

[a] 50% Growth inhibition and the values are mean of three determinations,
[b] brest cancer,
[c] ovary cancer,
[d] colon cancer,
[e] prostate cancer,
[f] cervix cancer,
[g] lung cancer,
[h] oral cancer,
ADR, adriamycin.

EXAMPLES

The following examples are given by way of illustration and therefore should not be construed to limit the scope of present invention in any way.

Example 1

7-Methoxy-8-[3-(4-{4-[3(1,3-benzothiaol-2-yl)-phenoxy]propyl}piperazin-1-yl)propyl]oxy(11aS)-1,2,3,11a-tetrahydro-5H-pyrrolo[2,1-c][1,4]benzodiazepin-5-one (9a).

To a solution of ((2S)-[N-{4-(3-(piperazin-1-yl)propyloxy)-5-methoxy-2-nitro benzoyl] pyrrolidine-2-carboxaldehydediethylthioacetal 4a {535 mg, 1 mmol} in acetone (10 mL) was added anhydrous K$_2$CO$_3$ (552 mg, 4 mmol) and the 4-[3(benzothiazol-2-yl)bromopropyloxy]phenol 6a (354 mg, 1 mmol). The reaction mixture was heated to reflux for 48 h. After completion of the reaction as indicated by TLC, potassium carbonate was removed by suction filtration and the solvent was removed under vacuum.

The crude product thus obtained was purified by column chromatography using ethylacetate-hexane (8:2) as eluant to afford pure compound of 7a (605 mg, 75%).

$^1$H NMR (CDCl$_3$.300 MHz): δ 8.02 (d, 2H, J=9.0 Hz), 7.83 (d, 1H, J=7.5 Hz), 7,61 (s, 1H), 7.42 (m, 1H, J=8.3 Hz), 7.31 (d, 2H, J=7.5 Hz), 6.94 (d, 2H, J=9.0 Hz), 6.81 (s, 1H ) 4.85 (d, 1H, J=3.7 Hz), 4.7 (m, 1H), 4.16-4.10 (m, 4H), 3.92 (s, 3H), 3.21-3.34 (m, 2H), 2.63-2.85 (m, 4H), 2.55 (m, 9H), 2.26 (m, 2H), 2.05 (m, 6H, J=6.04 Hz), 1.82 (m, 2H), 1.2-1.4 (m, 6H, J=6.79 Hz).

ESIMS: m/z 795(M+H)$^+$.

To compound 7a (682 mg, 1 mmol) in methanol (20 mL) was added SnCl$_2$.2H$_2$O (1.125 g, 5 mmol) and refluxed at 80° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 8a (525 mg, 80%), which was used directly in the next step.

A solution of 8a (652 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH-CHCl$_3$ (4%) to give compound 9a (367 mg, 60%). This material was repeatedly evaporated from CHCl$_3$ in vacuum to generate the imine form.

$^1$H NMR (CDCl$_3$. 300 MHz): δ 8.04 (d, 2H, J=8.8 Hz), 7.88 (d, 1H, J=8.0 Hz), 7.68 (d, 1H, J=4.5 Hz), 7.52 (s, 1H), 7.3-7.45 (m, 3H), 7.01 (d, 2H, J=8.8 Hz), 6.84 (s, 1H), 4.0-4.12 (m, 2H), 3.92 (s, 3H), 3.82-3.55 (m, 4H), 2.45-2.52 (m, 8H), 2.25-2.32 (m, 1H), 1.91-2.09 (m, 6H), 1.54-1.88 (m, 4H), 1.28-1.38 (m, 2H).

ESIMS: m/z 640 (M+H)$^+$, 671 (M$^+$+MeOH).

Example 2

7-Methoxy-8-[3-(4-{4-[3(1,3-benzothiazol-2-yl)-2-methoxyphenoxy]propyl}piperazin-1-yl) propyl] oxy-(11aS)-1,2,3,11a-tetrahydro-5H-pyrrolo[2,1-c] [1,4] benzodiazepin-5-one(9b).

To a solution of (2S)-[N-{4-(3-(piperazin-1-yl)propyloxy)-5-methoxy-2-nitro benzoyl] pyrrolidine-2-carboxaldehyde diethylthioacetal 4a (535 mg, 1 mmol) in acetone (10 mL) was added anhydrous K$_2$CO$_3$ (552 mg, 4 mmol) and 4-[3(benzothiazol-2-yl)bromopropyloxy]3-methoxyphenol 6b (384 mg, 1 mmol). The reaction mixture was heated to reflux for 48 h. After completion of the reaction as indicated by TLC, potassium carbonate was removed by suction filtration and the solvent was removed under vacuum.

The crude product thus obtained was purified by column chromatography using ethylacetate-hexane (8:2) as eluant to afford pure compound of 7b (628 mg) 75%.

$^1$H NMR (CDCl$_3$ 300 MHz): δ 8.01 (d, 1H, J=8.3 Hz), 7.89 (d, 1H, J=8.3 Hz), 7.75 (m, 2H), 7.55 (dd, 1H, J=7.5 Hz), 7.45 (t, 1H, J=8.3 Hz), 7.3 (t, 1H, J=8.0 Hz), 6.93 (d, 1H, J=8.3 Hz), 6.7 (s, 1H), 4.85 (d, 1H, J=3.7 Hz), 4.65 (m, 1H), 4.2 (m, 4H), 4.00 (s, 3H), 3.92 (s, 3H), 3.21-3.34 (m, 2H), 2.62-2.83 (m, 6H), 2.59-2.52 (m, 12H), 2.55 (m), 2.25 (m, 2H), 2.13-2.00 (m, 2H), 1.80 (m, 1H), 1.63-1.97 (m, 6H).

ESIMS: m/z 823 (M)$^+$.

To compound 7b (712 mg, 1 mmol) in methanol (20 mL) was added SnCl$_2$.2H$_2$O (1.125 g, 5 mmol) and refluxed at 80° C. for 5h. or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated, under vacuum to afford the crude amino diethylthioacetal 8b (514 mg, 75%), which was used directly in the next step.

A solution of 8b (682 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 ml), brine (20 mL) and the combined organic phase was dried (Na$_2$SO$_4$). The organic layer was evaporated under vacuum and purified by column chromatography using MeOH-CHCl$_3$ (5%) to give compound 9b (344 mg, 60%). This material was repeatedly evaporated from CHCl$_3$ in vacuum to generate the imine form.

$^1$H NMR (CDCl$_3$, 300 MHz): δ 8.02 (d, 1H, J=8.3 Hz), 7.88 (d, 1H, J=7.5 Hz), 7.71 (m, 2H), 7.65 (d, 1H, J=4.5 Hz), 7.55 (dd, 1H, J=7.5 Hz), 7.48 (d, 1H, J=7.5 Hz), 7.36 (m, 1H, J=6.7 Hz), 6.92 (d, 1H, J=8.3 Hz), 6.78 (s, 1H), 4.1-4.4 (m, 4H), 4.0 (s, 3H), 3.95 (s, 3H), 3.5-3.85 (m, 3H), 2.38-2.57 (m, 8H), 2.2-0.32 (m, 1H), 1.96-2.05 (m, 6H), 1.88-1.67 (m, 2H), 1.21-1.36 (m, 2H).

ESIMS:m/z 670 (M+H)$^+$.

Example 3

7-Methoxy-8-[3-(4-{4-[3(6-flouro-1,3-benzothiazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9c).

To a solution of (2S)-[N-{4-(3-(piperazin-1-yl)propyloxy)-5-methoxy-2-nitro benzoyl] pyrrolidine-2-carboxaldehyde diethylthioacetal 4a (549 mg, 1 mmol) in acetone (10 mL) was added anhydrous K$_2$CO$_3$ (552 mg, 4 mmol) and the 4-[3(6-fluorobenzothiazol-2-yl)bromopropyloxy]3-methoxyphenol 6c (382 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7c (612 mg, 75%).

$^1$H NMR (CDCl$_3$, 300 MHz): δ 7.91-8.02 (m, 3H, J=8.3, 9.0 Hz), 7.68 (s, 1H), 7.55 (dd, 1H, J=7.5 Hz), 7.20 (td, 1H, J=7.55 Hz), 6.95 (d, 2H, J=8.3 Hz), 6.75 (s, 1H), 4.85 (d, 1H, J=3.7 Hz), 4.75 (m, 1H), 4.15 (m, 4H), 3.92 (s, 3H), 3.21-3.34 (m, 2H), 2.63-2.85 (m, 4H), 2.55 (m, 12H)) 2.25 (m, 2H), 2.05 (m, 5H), 1.6-1.8 (m. 3H), 1.35 (q, 6H, J=6.79 Hz).

ESIMS: m/z 783 (M+H)$^+$.

To compound 7c (696 mg, 1 mmol) in methanol (20 mL) was added SnCl$_2$.2H$_2$O (1.125 g; 5 mmol) and refluxed at 80° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethyl thioacetal 8c (535 mg, 80%), which was used directly in the next step.

A solution of 8c (666 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH-CHCl$_3$ (4%) to give compound 9c (350 mg, 60%). This material was repeatedly evaporated from CHCl$_3$ in vacuum to generate the imine form.

$^1$H NMR (CDCl$_3$, 300 MHz): δ 7.91-8.0 (m, 3H, J=8.3, 9.0 Hz), 7.64 (d,1H, J=4.7 Hz), 7.55 (dd, 1H, J=7.5 Hz), 7.50 (s, 1H), 7.20 (td, 1H, J=7.5 Hz), 6.95 (d, 2H, J=8.3 Hz), 6.75 (s, 1H), 4.12 (m, 4H), 3.92 (s, 3H), 3.82-3.52 (m, 3H), 2.55-2.52 (m, 8H), 2.32 (t, 2H), 2.09 (m, 6H), 1.88 (m, 2H), 1.38 (m, 2H).

ESIMS: m/z 658 (M+H)$^+$.

Example 4

7-Methoxy-8-[3-(4-{3-[3(1,3-benzothiazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9d).

To a solution of (2S)-[N-{4-(3-(piperazin-1-yl)propyloxy)-5-methoxy-2-nitro benzoyl] pyrrolidine-2-carboxaldehyde diethylthioacetal 4a (549 mg, 1 mmol) in acetone (10 mL) was added anhydrous K$_2$CO$_3$ (552 mg, 4 mmol) and the 3-[3(benzothiazol-2-yl)bromopropyloxy]phenol 6d (363 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7d (580 mg, 70%).

$^1$H NMR (CDCl$_3$): δ 8.03 (d, 1H, J=8.309 Hz), 7.85 (d, 1H, J=8.309 Hz), 7.69 (d, 1H, J=1.6 Hz), 7.59 (d, 1H, J=8.309 ), 7.45 (dt, 1H, J=7.554 Hz), 7.33 (dt, 1H, J=8.309 Hz), 6.92 (d, 1H, J=8.309 Hz), 6.78 (s, 1H), 4.85 (d, 1H, J=3.77 Hz), 4.65 (m, 1H), 4.25 (m, 4H, J=6.043 ), 3.92(s, 3H), 3.12 (m, 2H), 2.6-2.8 (m, 4H), 2.28 (m), 1.80 (m, 10H), 1.2-1.4 (m, 6H).

ESIMS: m/z 795 (M+H)$^+$.

To compound 7d (726 mg, 1 mmol) in methanol (20 mL) was added SnCl$_2$.2H$_2$O (1.125 g, 5 mmol) and refluxed at 80° C. for 5 h or until the TLC indicated that reaction was completed. The methanol was evaporated under vacuum; the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethyl thioacetal 8d (559 mg, 80%), which was used directly in the next step.

A solution of 8d (696 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SCO$_4$). The organic layer was evaporated under vacuum and purified by column chromatography using MeOH—CHCl$_3$ (5%) to give compound 9d (320 mg, 55%). This material was repeatedly evaporated from CHCl$_3$ in vacuum to generate the imine form.

$^1$H NMR (CDCl$_3$): 8.03 (d, 1H, J=8.309 Hz), 7.85 (d, 1H, J=8.309 Hz), 7.69 (d, 1H, J=4.52 Hz), 7.59 (d, 1H, J=8.309 ), 7.45 (dt, 1H, J=7.554 Hz), 7.33 (dt, 1H, J=8.309 Hz), 6.92 (d, 1H, J=8.309 Hz), 6.78 (s, 1H), 4.85 (d, 1H, J=3.77 Hz), 4.12 (m), 3.92 (s, 3H), 3.82 (m), 3.71 (m), 3.55 (m), 2.52 (m), 2.32 (m),2.09 (t), 1.88 (m), 1.38 (m).

ESIMS: m/z 641 (M+H)$^+$.

Example 5

7-Methoxy-8-[4-(4-{4-[4(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9e).

To a solution of (2S)-[N-{4-(4-(piperazin-1-yl)butyloxy)-5-methoxy-2-nitro benzoyl]pyrrolidine-2-carboxaldehyde diethylthioacetal 4b (549 mg, 1 mmol) in acetone (10 mL) was added anhydrous $K_2CO_3$ (552 mg, 4 mmol) and 4-[4(benzothiazol-2-yl)bromobutyloxy]phenol 6e (368 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7e (668 mg, 80%).

$^1$H NMR (CDCl$_3$ 300 MHz): δ 8.05 (d, 2H, J=9.0 Hz), 7.83 (d, 1H, J=7.5 Hz), 7.61 (s, 1H), 7.42 (m, 1H, J=8.3 Hz), 7.31 (m, 2H, J=7.5 Hz), 6.94 (d, 2H, J=9.0 Hz), 6.81 (s, 1H), 4.89 (d, 1H, J=3.7 Hz), 4.65 (m, 1H), 4.17 (m, 4H, J=6.4 Hz), 3.92 (s, 3H), 3.23 (m, 2H), 2.52-2.8 (m, 14H), 2.27 (m, 2H), 2.31 (m, 2H), 2.12 (m, 2H), 1.63-1.97 (m, 10H), 1.39 (q, 6H, J=6.79 Hz).

ESIMS: m/z 823 (M+H)$^+$.

To compound 7e (665 mg, 1 mmol) in methanol (20 mL) was added $SnCl_2.2H_2O$ (1.125 g, 5 mmol) and refluxed at 80° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 8e which was used directly in the next step.

A solution of 8e (649 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 9e (273 mg, 50%). This material was repeatedly evaporated from CHCl$_3$ in vacuum to generate the imine form.

$^1$H NMR (CDCl$_3$, 300 MHz): δ 8.04 (d, 2H, J=6.7 Hz), 7.88 (d, 1H, J=7.5 Hz), 7.68 (d, 1H, J=4.5 Hz), 7.52 (m, 2H), 7.41-7.48 (m, 2H, J=8.3 Hz), 7.01 (d, 2H, J=9.0 Hz), 6.89 (s, 1H), 4.21-4.12 (m, 4H), 3.90 (s, 3H), 3.58-3.8 (m, 3H), 2.52-2.45 (m, 8H), 2.30-2.32 (m, 2H), 1.90-2.04 (m, 2H), 1.7-1.88 (m, 4H), 1.52-1.67 (m, 6H), 1.32-1.34 (m, 2H).

ESIMS: m/z 668 (M+H)$^+$.

Example 6

7-Methoxy-8-[4-(4-{4-[4(1,3-benzothiazol-2-yl)-2-methoxyphenoxy]butyl}piperazin-1-yl) butyl]oxy-(11aS)-1,2,3,11a-tetrahydro-5H-pyrrolo[2,1-c][1,4]benzodiazepin-5-one (9f).

To a solution of (2S)-[N-{4-(4-(piperazin-1-yl)butyloxy)-5-methoxy-2-nitro benzoyl]pyrrolidine-2-carboxaldehyde diethylthioacetal 4b (549 mg, 1 mmol) in acetone (10 mL) was added anhydrous $K_2CO_3$ (552 mg, 4 mmol) and the 4-[4(benzothiazol-2-yl)bromobutyloxy]3-methoxyphenol 6f (398 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7f (649 mg, 75%).

$^1$H NMR (CDCl$_3$ 300 MHz): δ 8.01 (d, 1H, J=8.3 Hz), 7.75 (m, 2H), 7.63(s, 1H), 7.52 (dd, 1H, J=8.0, 1.6 Hz), 7.45-7.3 (d, 2H, J=8.3 Hz), 6.95 (d, 1H, J=8.3 Hz), 6.75 (s, 1H), 4.89 (d, 1H, J=3.7 Hz), 4.65 (m, 1H), 4.71 (m, 4H), 4.02 (s, 3H), 3.94 (s, 3H), 3.23 (m, 2H), 2.6-2.8 (m, 14H), 2.57 (m, 2H J=6.04 Hz), 2.31 (m, 2H), 2.12 (m, 2H), 1.6-1.97 (m, 10H), 1.35 (q, 6H, J=7.6 Hz).

ESIMS: m/z 852 (M+H)$^+$.

To compound 7f(695 mg, 1 mmol) in methanol (20 mL) was added $SnCl_2.2H_2O$ (1.125 g, 5 mmol) and refluxed at 80° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 8f which was used directly in the next step.

A solution of 8f (679 mg, 1 mmol), HgCl2 (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 9f (281 mg, 50%). This material was repeatedly evaporated from CHCl$_3$ in vacuum to generate the imine form.

$^1$H NMR (CDCl$_3$, 200 MHz): δ 8.02 (d, 1H, J=8.3 Hz), 7.71-7.86 (d, 3H, J=7.5 Hz), 7.65 (d, 1H, J=4.5 Hz), 7.55 (dd, 1H, J=7,5 Hz), 7.46 (d, 1H, J=7.5 Hz), 7.36 (m, 1H, J=6.7 Hz), 6.94 (d, 1H, J=8.3 Hz), 6.8 (s, 1H), 4.22-4.16 (m, 4H, J=6.0 Hz), 4.01 (s, 3H), 3.92 (s, 3H), 3.55-3.82 (m, 3H), 2.38-2.57 (m, 8H), 2.29-2.34 (m, 2H), 2.04-2.1 (m, 2H), 1.6-1.86 (m, 4H), 1.53-1.64 (m, 6H), 1.34-1.38 (m, 2H).

ESIMS: m/z 698 (M+H)$^+$.

Example 7

7-Methoxy-8-[4-(4-{4-[4(6-fluoro-1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9g).

To a solution of 4b (400 mg, 1 mmol) in acetone (10 mL) was added anhydrous $K_2CO_3$(552 mg, 4 mmol) and the 6 g (276 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7 g (435 mg, 70%).

$^1$H NMR (CDCl$_3$, 300 MHz): δ 7.91-7.98 (m, 3H, J=8.3, 9.0 Hz), 7.68 (s, 1H), 7.54 (dd, 1H, J=7.5, 2.2 Hz), 7.18 (d,

1H, J=7.5 Hz), 6.96 (d, 2H, J=8.30 Hz), 6.75 (s, 1H) 4.89 (d, 1H, J=3.77 Hz), 4.65 (m, 1H), 4.17 (m, 4H, J=6.40 Hz), 3.92 (s, 3H), 3.23 (m, 2H), 2.52-2.8 (m, 14H), 2.54 (m, 2H), 2.31 (m, 2H), 2.10 (m, 2H), 1.63-1.97 (m, 10H), 1.39 (q, 6H, J=6.79 Hz). ESIMS: m/z 841 (M+H)⁺.

To compound 7 g (709 mg, 1 mmol) in methanol (20 mL) was added SnCl₂.2H₂O (1.125 g, 5 mmol) and refluxed at 80° C. for 5 h or until the TLC indicated that reaction was completed. The methanol was evaporated under vacuum; the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethylthioacetal 8 g which was used directly in the next step.

A solution of 8 g (679 mg, 1 mmol), HgCl₂ (613 mg, 2.26 mmol) and CaCO₃ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 9 g (344 mg, 60%). This material was repeatedly evaporated from CHCl₃ in vacuum to generate the imine form.

¹H NMR (CDCl₃ 300 MHz): δ 7.92-8.04 (m, 3H, J=8.3, 9.0 Hz), 7.65 (d, 1H, J=4.3 Hz), 7.54 (dd, 2H, J=7.5 Hz ), 7.22 (td, 1H, J=7.5 Hz), 6.96 (d, 2H, J=8.3 Hz), 6.8 (s, 1H), 4.23-4.12 (m, 4H), 3.90 (s, 3H), 3.55-3.8 (m, 3H), 2.52-2.45 (m, 8H), 2.30-2.32 (m, 4H), 2.12-2.04 (m, 2H), 1.65-1.88 (m, 6H), 1.45-1.35 (m. 2H).

ESIMS: m/z 686 (M+H)¹.

Example 8

7-Methoxy-8-[4-(4-{4-[3(1,3-benzothiazol-2-yl)-phenoxy]butyl}piperazin-1-yl)butyl]oxy-(11aS) -1,2,3,11a-tetrahydro-5H-pyrrolo[2,1-c][1,4]benzodiazepin-5-one (9h).

To a solution of 4b (400 mg, 1 mmol) in acetone (10 mL) was added anhydrous K₂CO₃ (552 mg, 4 mmol) and the 6h (268 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7h (456 mg, 75%).

¹H NMR (CDCl₃): δ 8.03 (d, 1H, J=8.309 Hz), 7.89 (d, J=8.309 Hz ), 7.69 (s, 1H), 7.59 (d, 1H, J=8.309 Hz), 7.45 (m, J=7.554 Hz),7.35 (m, J=8.309 Hz), 6.92 (dd, J=8.309 Hz), 6.78 (s), 4.82 (d, J=3.77 Hz), 4.65 (m), 4.2 (m, J=6.04 Hz), 3.92 (s, 3H), 3.23 (m), 2.62-2.83 (m), 2.57 (m, J=6.043 Hz ), 2.31 (m), 2.12 (m), 1.63-1.97 (m), 1.38 (m, J=6.798 Hz). ESIMS: m/z 823 (M)*.

To compound 7h (727 mg, 1 mmol) in methanol (20 mL) was added SnCl₂.2H₂O (1.125 g, 5 mmol) and refluxed at 80° C. for 5 h or until the TLC indicated that reaction was completed. The methanol was evaporated under vacuum, the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethylthioacetal 8h, which was used directly in the next step.

A solution of 8h(697 mg, 1 mmol), HgCl₂ (613 mg, 2.26 mmol) and CaCO₃ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 9h (322 mg, 55%). This material was repeatedly evaporated from CHCl₃ in vacuum to generate the imine form.

¹H NMR (CDCl₃): 8.03 (d, 1H, J=8.309 Hz), 7.85 (d, 1H, J=8.309 Hz), 7.69 (d, 1H, J=4.532 Hz), 7.59 (d, 1H, J=8.309), 7.45 (dt, 1H, J=7.554 Hz), 7.33 (dt, 1H, J=8.309 Hz), 6.92 (d, 1H, J=8.309 Hz), 6.78 (s, 1H), 4.12 (m, 4H), 3.90 (s, 3H), 3.8 (m, 3H), 3.71 (m, 2H), 3.55 (m), 2.52 (m), 2.45 (m), 2.32 (m), 2.04 (m), 1.88 (m), 1.67 (m), 1.34 (m). ESIMS: m/z 668 (M+H)⁺.

Example 9

7-Methoxy-8-[3-(4-{4-[3(1,3-benzoxazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9i).

To a solution of (2S)-[N-{4-(3-(piperazin-1-yl)propyloxy)-5-methoxy-2-nitro benzoyl] pyrrolidine-2-carboxaldehyde diethylthioacetal 4a (549 mg, 1 mmol) in acetone (10 mL) was added anhydrous K₂CO₃ (552 mg, 4 mmol) and the 4-[3(benzoxazol-2-yl)bromopropyloxy]phenol 6i (346 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (8:2) as eluant to afford pure compound of 7i (631 mg, 75%).

¹H NMR (CDCl₃ 300 MHz): δ 7.85 (d, 1H, J=7.5 Hz), 7.78 (m, 1H, J=9.0 Hz), 7.71 (m, 2H), 7.57 (m, 1H, J=8.3 Hz), 7.45 (t, 1H, J=7.4 Hz), 7.38 (t, 1H, J=9.0 Hz), 7.01 (d, 2H, J=7.5 Hz), 6.82 (s, 1H), 4.86 (d, 1H, J=3.7 Hz), 4.73 (m, 1H), 4.18 (m, 4H, J=6.0 Hz), 3.94 (s, 3H), 3.29 (m, 2H), 2.54-2.83 (m, 14H), 2.27 (m, 2H), 2.13-1.73 (m, 12H), 1.36 (t, 6H, J=6.79 Hz). ESIMS: m/z 778 (M+H)⁺.

To compound 7i (695 mg, 1 mmol) in methanol (20 ml) was added SnCl₂.2H₂O (1.125 g, 5 mmol) and refluxed at 80° C. for 5 h or until the TLC indicated that reaction was ompleted. The methanol was evaporated under vacuum, the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethylthioacetal 8i which was used directly in the next step.

A solution of 8i (679 mg, 1 mmol), HgCl₂ (613 mg, 2.26 mmol) and CaCO₃ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 9i (334 mg, 55%). This material was repeatedly evaporated from CHCl₂ in vacuum to generate the imine form.

¹H NMR (CDCl₃ 300 MHz): δ 8.2 (d, 2H, J=8.3 Hz), 7.86 (d, 1H, J=7.5 Hz), 7.65 (d, 1H, J=4.5 Hz), 7.55 (dd, 2H, J=7.5 Hz), 7.48 (d, 1H), 7.36 (m, 1H, J=6.7 Hz), 6.92 (d, 2H, J=8.3 Hz), 6.78 (s, 1H), 4.19-4.13 (m, 4H, J=6.0 Hz), 3.92 (s, 3H), 3.54-3.82 (m, 4H), 2.38-2.57 (m, 8H),.2.32 (m, 2H), 2.04-2.15 (m, 4H), 1.67-1.88 (m, 8H) 1.30-1.38 (m, 2H). ESIMS: m/z 698 (M+H)⁺.

Example 10

7-Methoxy-8-[3-(4-{4-[3(1,3-benzoxazol-2-yl)-2-methoxyphenoxy]propyl}piperazin-1-yl)propyl]oxy-(11aS)-1,2,3,11a-tetrahydro-5H-pyrrolo[2,1-c][1,4]benzodiazepin-5-one (9j).

To a solution of (2S)-[N-{4-(3-(piperazin-1-yl)propyl)-5-methoxy-2-nitrobenzoyl] pyrrolidine-2-carboxaldehyde diethylthioacetal 4a (535 mg, 1 mmol) in acetone (10 mL) was added anhydrous K₂CO₃ (552 mg, 4 mmol).and 4-[3 (benzoxazol-2-yl)bromopropaxy]-3-methoxyphenol 6j (384 mg, 1 mmol). The reaction mixture was heated to reflux for 48 h. After completion of the reaction as indicated by TLC, potassium carbonate was removed by suction filtration and the solvent was removed under vacuum.

The crude product thus obtained was purified by column chromatography using ethylacetate- hexane (7:2) as eluant to afford pure compound of 7j (616 mg) 75%.

¹H NMR (CDCl₃ 300 MHz): δ 7.85 (d, 1H, J=8.3 Hz), 7.78 (d, 1H, J=8.3 Hz), 7.71 (s, 1H) 7.57 (m, 2H, J=9.0 Hz), 7.36 (dd, 2H, J=9.0 Hz), 6.93 (d, 1H, J=8.3 Hz), 6.82 (s, 1H), 4.85 (d, 1H, J=3.7 Hz), 4.71 (m, 1H), 4.19 (m, 4H, J=6.0 Hz), 4.04 (s, 3H), 3.92 (s, 3H), 3.26 (m, 2H), 2.71-2.43 (m, 16H), 2.28 (m, 2H), 2.05 (m), 1.63-2.14 (m, 8H), 1.38 (t, 6H). ESIMS: m/z 809 (M+H)¹.

To compound 7j(712 mg, 1 mmol) in methanol (20 ml) was added SnCl₂.2H₂O (1.125 g, 5 mmol) and refluxed at 80° C. for 5 h or until the TLC indicated that reaction was completed. The methanol was evaporated under vacuum, the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethylthioacetal 8j (511 mg, 75%), which was used directly in the next step.

A solution of 8j (682 mg, 1 mmol), HgCl₂ (613 mg, 2.26 mmol) and CaCO₃ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 9j (320 mg, 56%). This material was repeatedly evaporated from CHCl₃ in vacuum to generate the imine form.

¹H NMR (CDCl₃ 200 MHz): δ 7.85 (d, 1H, J=8.3 Hz), 7.78 (d, 1H, J=7.5 Hz), 7.71 (m, 2H), 7.65 (d, 1H, J=4.5Hz), 7.51 (dd, 1H, J=7.5 Hz), 7.38 (m, 1H, J=7.5 Hz), 7.36 (m, 1H, J=6.7 Hz), 6.92 (d, 2H, J=8.3 Hz), 6.78 (s, 1H), 4.1-4.4 (m, 4H), 4.04 (s, 3H), 3.9 (s, 3H), 3.5-3.85 (m, 4H), 2.38-2.57 (m, 8H), 2.32 (t, 2H), 2.05 (t, 2H), 1.88-1.66 (m, 4H), 1.38 (m, 2H). ESIMS: m/z 654 (M+H)⁺.

Example 11

7-Methoxy-8-[3-(4-{3-[3(1,3-benzoxazol-2-yl)-phenoxy]propyl}piperazin-1-yl)propyl]oxy-(11aS)-1,2,3,11a-tetrahydro-5H-pyrrolo[2,1-c][1,4]benzodiazepin-5-one (9k).

To a solution of (2S)-[N-{4-(3-(piperazin-1-yl)propyl)-5-methoxy-2-nitrobenzoyl] pyrrolidine-2-carboxaldehyde diethylthioacetal 4a (549 mg, 1 mmol) in acetone (10 mL) was added anhydrous K₂CO₃ (552 mg, 4 mmol) and the 3-[3(benzoxazol-2-yl)bromopropaxy]phenol 6k (346 mg, 1 mmol). The reaction mixture was heated to reflux for 48 h. After completion of the reaction as indicated by TLC, potassium carbonate was removed by suction filtration and the solvent was removed under vacuum.

The crude product thus obtained was purified by column chromatography using ethylacetate-hexane (7:2) as eluant to afford pure compound of 7k (568 mg, 70%).

¹H NMR (COCl₃): δ 7.85 (d, 1H, J=7.654 Hz), 7.78 (d, 1H, J=8.309 Hz), 7.71 (d, 1H, J=1.6 Hz), 7.57 (d, 1H, J=8.309 ), 7.45 (dt, 1H, J=7.554 Hz), 7.38 (dt, 1H, J=8.309 Hz), 7.01 (d, 1H, J=8.309 Hz), 6.82 (s, 1H), 4.85 (d, 1H, J=3.77 Hz), 4.7. (m, 1H), 4.20 (m, 4H, J=6.043 ), 3.92 (s, 3H), 3.36 (m, 2H), 2.6-2.8 (m, 4H), 2.49 (m), 1.80 (m, 10H), 1.2-1.4 (m, 6H). ESIMS: m/z 778 (M+H)⁺.

To compound 7k (726 mg, 1 mmol) in methanol(20 mL) was added SnCl₂.2H₂O (1.125 g, 5 mmol) and refluxed at 80° C. for 5 h or until the TLC indicated that reaction was completed. The methanol was evaporated under vacuum; the aqueous layer was then carefully adjusted to pH 8 with 10% NaHCO₃ solution and then extracted with ethyl acetate and chloroform (2×30 mL and 2×30 mL). The combined organic phase was dried over Na₂SO₄ and evaporated under vacuum to afford the crude amino diethyl thioacetal 8k (557 mg, 80%), which was used directly in the next step.

A solution of 8k (696 mg, 1 mmol), HgCl₂ (613 mg, 2.26 mmol) and CaCO₃ (246 mg, 2.46 mmol) in acetonitrile-water (4:1) was stirred slowly at 27° C. for 12h. The reaction mixture was diluted with ethyl acetate (30 mL) filtered through a celite pad. The clear organic supernatant was extracted with saturated 5% NaHCO₃ (20 mL), brine (20 mL) and the combined organic phase was dried (Na₂SO₄). The organic layer was evaporated under vacuum and purified by column chromatography using MeOH—CHCl₃ (5%) to give compound 9k (368 mg, 55%). This material was repeatedly evaporated from CHCl₃ in vacuum to generate the imine form.

¹H NMR (CDCl₃): 7.85 (d, 1H, J=8.309 Hz), 7.78 (d, 1H, J=8.309 Hz), 7.65 (d, 1H, J=4.52 Hz), 7.59 (d, 1H, J=8.309 ), 7.45 (dt, 1H, J=7.554 Hz), 7.33 (dt, 1H, J=8.309 Hz), 6.92 (d, 1H, J=8.309 Hz), 6.78 (s, 1H), 4.85 (d, 1H, J=3.77 Hz), 4.12 (m), 3.92 (s, 3H), 3.82 (m), 3.71 (m), 3.55 (m), 2.52 (m), 2.32 (m),2.09 (t), 1.88 (m), 1.38 (m). ESIMS: m/z 624 (M+H)⁺.

Example 12

7-Methoxy-8-[4-(4-{4-[4(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one (9l).

To a solution of (2S)-[N-(4-(4-(piperazin-1-yl)butyloxy)-5-methoxy-2-nitro benzoyl]pyrrolidine-2-carboxaldehyde diethylthioacetal 4b (549 mg, 1 mmol) in acetone (10 mL) was added anhydrous K₂CO₃ (552 mg, 4 mmol) and 4-[4

(benzoxazol-2-yl)bromobutyl]phenol 6l (351 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (7:3) as eluant to afford, pure compound of 7l (655 mg, 80%).

$^1$H NMR (CDCl$_3$ 300 MHz): δ 7.85 (d, 2H, J=7.6 Hz), 7.78 (d, 1H, J=9.0 Hz), 7.71 (s, 1H), 7.57 (m, 1H, J=8.3 Hz), 7.45 (m, 2H, J=7.5Hz), 7.01 (d, 2H, J=7.5 Hz), 6.81 (s, 1H), 4.89 (d, 1H, J=3.7 Hz), 4.65 (m, 1H), 4.16 (m, 4H, J=6.4 Hz), 3.92 (s, 3H), 3.23 (m, 2H), 2.52-2.8 (m, 14H), 2.31 (m, 2H), 2.12 (m, 2H), 1.63-1.97 (m, 10H), 1.39 (q, 6H, J=6.79 Hz). ESIMS: m/z 807 (M+H)$^+$.

To compound 7l (665 mg, 1 mmol) in methanol (20 mL) was added SnCl$_2$.2H$_2$O (1.125 g, 5 mmol) and refluxed at 80° C for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 8l which was used directly in the next step.

A solution of 8l (649 mg, 1 mmol), HgCl$_2$ (613 mg, 2.26 mmol) and CaCO$_3$ (246 mg, 2.46 mmol) in acetonitrile-water (4:1) was stirred slowly at 27° C for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 9l (299 mg) 55%). This material was repeatedly evaporated from CHCl3 in vacuum to generate the imine form.

$^1$H NMR (CDCl$_3$ 300 MHz): δ 7.85 (d, 1H, J=6.7 Hz), 7.81 (d, 1H, J=7.5 Hz), 7.76 (d, 1H, J=4.54 Hz), 7.72 (m, 1H), 7.68 (d, 1H, J=4.5 Hz), 7.52-7.58 (m, 2H, J=9.06 Hz), 7.50 (s, 1H), 7.38 (td, 1H), 7.02 (d, 1H), 6.8 (s, 1H), 4.05-4.1 (m, 4H), 3.90 (s, 3H), 3.51-3.8 (m, 4H), 2.52-2.45 (m, 8H), 2.32 (m, 2H), 2:04 (m, 6H), 1.88-1.6 (m, 4H), 1.34 (m, 2H). ESIMS: m/z 653 (M+H)$^+$.

Example 13

7-Methoxy-8-[4-(4-{4-[4(1,3-benzothiazol-2-yl)-2-methoxyphenoxy]butyl}piperazin-1-yl)butyl]oxy-(11aS)-1,2,3,11a-tetrahydro-5H-pyrrolo[2,1-c][1,4]benzodiazepin-5-one (9m).

To a solution of (2S )-[N-{4-(4-(piperazin-1-yl)butyl)-5-methoxy-2-nitrobenzoyl]pyrrolidine-2-carboxaldehyde diethylthioacetal 4b (549 mg, 1 mmol) in acetone (10 mL) was added anhydrous K$_2$CO$_3$ (552 mg, 4 mmol) and the 4-[4(benzoxazol-2-yl)bromobutyl]3-methoxyphenol 6m (382 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (7:1) as eluant to afford pure compound of 7m (637 mg, 75%).

$^1$H NMR (CDCl$_3$ 300 MHz): δ 7.75-7.89 (m, 3H, J=8.30 Hz), 7.71 (s, 1H), 7.52 (m, 1H), 7.36 (m, 1H, J=9.0 Hz), 7.01 (d, 2H, J=8.3 Hz), 6.82 (s, 1H), 4.89 (d, 1H, J=3.7 Hz), 4.65 (m, 1H), 4.71 (m, 4H), 4.02 (s, 3H), 3.94 (s, 3H), 3.23 (m, 2H), 2.6-2.8 (m, 14H), 2.57 (m, 2H, J=6.04 Hz), 2.31 (m, 2H), 2.12 (m, 2H), 1.6-1.97 (m, 10H), 1.35 (q, 6H, J =7.6 Hz). ESIMS: m/z 837(M+H)$^+$.

To compound 7m (695 mg, 1 mmol) in methanol (20 mL) was added SnCl$_2$.2H$_2$O (1.125 g, 5 mmol) and refluxed at 80° C. for 5h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 8m, which was used directly in the next step.

A solution of 8m (679 mg, 1 mmol), HgCl$_2$ (613 mg, 2.26 mmol) and CaCO$_3$ (246 mg, 2.46 mmol) in acetonitrile-water (4:1) was stirred slowly at 27° C for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 9m (287 mg, 50%). This material was repeatedly evaporated from CHCl$_3$ in vacuum to generate the imine form.

$^1$H NMR (CDCl$_3$ 300 MHz): δ 7.85 (d, 1H, J=8.3 Hz), 7.76 (d, 1H, J=7.5 Hz), 7.71 (d, 1H), 7.68 (d, 1H, J=4.5 Hz), 7.36 (dd, 1H, J=7.5 Hz), 7.05-7.01 (m, 2H, J=6.7 Hz), 6.92 (d, 2H, J=8.3 Hz), 6.79 (s, 1H), 4.21-4.15 (m, 4H, J=6.0 Hz), 4.01 (s, 3H), 3.92 (s, 3H), 3.54-3.82 (m, 3H), 2.38-2.57 (m, 8H), 2.34 (m, 2H), 2.12-2.04 (m, 6H), 1.52-1.88 (m, 6H), 1.36-1.38 (m, 2H). ESIMS: m/z 683 (M+H)$^+$.

Example 14

7-Methoxy-8-[4-(4-{4-[3(1,3-benzothiazol-2-yl)-phenoxy]butyl}piperazin-1-yl)butyl]oxy-(11aS)-1,2,3,11a-tetrahydro-5H-pyrrolo[2,1-c][1,4]benzodiazepin-5-one(9m).

To a solution of 4b (400 mg, 1 mmol) in acetone (10 mL) was added anhydrous K$_2$CO$_3$ (552 mg, 4 mmol) and the 6n (256 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using ethylacetate-hexane (7:2) as eluant to afford pure compound of 7n (447 mg, 75%).

$^1$H NMR (CDCl$_3$): δ 7.85 (d, 1H, J=8.309 Hz), 7.78 (d, J=8.309 Hz ), 7.71 (s, 1H), 7.59 (d, 1H, J=8.309 Hz), 7.53 (m, J=7.554 Hz), 7.45(m, J=8.309 Hz),7.38 (m), 7.01 (d 2H) 6 (s, 1H), 4.82 (d, J=3.77 Hz), 4.65 (m), 4.2 (m, J=6.04 Hz), 3.92 (s, 3H), 3.23 (m), 2.62-2.83 (m), 2.57 (m, J=6.043 Hz ), 2.31 (m), 2.12 (m), 1.63-1.97 (m), 1.38 (m, J=6.798 Hz). ESIMS: m/z 807 (M)$^+$.

To compound 7n (727 mg, 1 mmol) in methanol (20 mL) was added SnCl$_2$.2H$_2$O (1.125 g, 5 mmol) and refluxed at 80° C. for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethylthioacetal 8n, which was used directly in the next step.

A solution of 8n(697 mg, 1 mmol), HgCl$_2$ (613 mg, 2.26 mmol) and CaCO$_3$ (246 mg, 2.46 mmol) in acetonitrile-water (4:1) was stirred slowly at 27° C. for 12 h. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (5%) to give compound 9n (315 mg, 55%). This material was repeatedly evaporated from CHCl3 in vacuum to generate the imine form.

$^1$H NMR (CDCl$_3$): 7.85 (d, 1H, J=8.309 Hz), 7.75 (d, 1H, J=8.309 Hz), 7.69 (d, 1H, J=1.6 Hz), 7.59 (d, 1H, J=8.309 ), 7.45 (dt, 1H, J=7.554 Hz), 7.33 (dt, 1H, J=8.309 Hz), 6.92 (d, 1H, J=8.309 Hz), 6.78 (s, 1H), 4.12 (m, 4H), 3.90 (s, 3H), 3.8 (m, 3H), 3.71 (m, 2H), 3.55 (m),2.52 (m), 2.45 (m), 2.32 (m), 2.04 (m), 1.88 (m), 1.67 (m), 1.34 (m). ESIMS: m/z 652 (M+H)$^+$.

Biological Activity

DNA Binding Affinity of Novel Benzothiazole, Benzoxazole Linked PBD Hybrids (9a-h)

Compounds have been subjected to thermal denaturation studies with duplex-form calf thymus DNA (CT-DNA) using an modification of a reported procedure (Newman, M. S. Carcinog-compr. Surv. 1976,1, 203; (b) Hecht, S. S.; Loy, M.; Hoffman, Carcinog-compr. Surv. 1976, 1, 325). Working solutions in aqueous buffer (10 mM NaH$_2$PO$_4$/Na$_2$HPO$_4$, 1 mM Na$_2$EDTA, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 using a Beckman DU-800 spectrophotometer fitted with high performance temperature controller, and heated at 1° C. min$^{-1}$ in the 40-110° C. range. DNA helix→coil transition temperatures (T$_m$) have been obtained from the maxima in the d(A$_{260}$)/dT derivative plots. Drug-induced alterations in DNA melting behavior are given by: ΔT$_m$=T$_m$(DNA+PBD)-T$_m$(DNA alone), where the T$_m$ value for the PBD-free CT-DNA is 69.1±0.01. The fixed [PBD]/[DNA]ratio used has not resulted in binding saturation of the host DNA duplex for any compound examined.

The DNA binding activity for these novel C8-linked benzothiazole, benzoxazole-PBD hybrids has been examined by thermal denaturation studies using calf thymus (CT) DNA. Melting studies show that these compounds stabilize the thermal helix→coil or melting stabilization (ΔT$_m$) for the CT-DNA duplex at pH 7.0, incubated at 37° C., where PBD/DNA molar ratio is 1:5. The data for the compounds 9a-n is included in Table 7 for comparison.

TABLE 7

Thermal denaturation data for benzothiazole and benzoxazle linked PBD hybrids with calf thymus (CT) DNA

| PBD hybrids | [PBD]:[DNA] molar ratio[b] | (ΔT$_m$ ° C.)[a] after incubation at 37° C. for | |
|---|---|---|---|
| | | 0 h | 18 h |
| 9a | 1:5 | 10.2 | 10.8 |
| 9b | 1:5 | 12.1 | 12.7 |
| 9c | 1:5 | 10.3 | 10.7 |
| 9d | 1:5 | 11.2 | 11.5 |
| 9e | 1:5 | 12.2 | 12.6 |
| 9f | 1:5 | 15.5 | 15.9 |
| 9g | 1:5 | 12.3 | 12.6 |
| 9h | 1:5 | 11.9 | 12.3 |
| 9i | 1:5 | 9.5 | 9.7 |
| 9j | 1:5 | 10.1 | 10.3 |
| 9k | 1:5 | 9.7 | 10.2 |
| 9l | 1:5 | 11.5 | 11.8 |
| 9m | 1:5 | 12.1 | 12.5 |
| 9n | 1:5 | 10.3 | 10.6 |
| DC-81 | 1:5 | 0.3 | 0.7 |

[a]For CT-DNA alone at pH 7.00 ± 0.01, T$_m$ = 69.1° C. ± 0.01 (mean value from 10 separate determinations), all ΔT$_m$ values are ±0.1-0.2° C.

[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

Anticancer activity: In vitro biological activity studies were carried out at the Advance Center for Treatment Research & Education in Cancer (ACTREC), Navi Mumbai.

The compounds were evaluated for in vitro anticancer activity against eight tumour cells lines derived from seven cancer types (non-small-cell lung, colon, oral, cervix, ovarian, prostate, and breast cancer) as shown in Table 2. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50) and 50% cell death (LC$_{50}$, −50% growth) compared with the control was calculated. Compounds 9a-9l have been evaluated for their in vitro cytotoxicity in eight cell lines from seven human cancer types of lung (Hop-62, A-549) colon (COLO-205) cervix (Si—Ha), ovary (A-2780), prostate (PC3) breast (MCF7), oral (KB). The results are expressed as percent of cell growth determined relative to that of untreated control cells (Table-8 and table-9).

TABLE 8

GI$_{50}$ (concentration in μM) values for the representative compounds 9a-I against human tumour cell lines.

| Cell Type | 9a GI$_{50}$ | 9b GI$_{50}$ | 9c GI$_{50}$ | 9d GI$_{50}$ | 9e GI$_{50}$ | 9f GI$_{50}$ | 9g GI$_{50}$ | 9h GI$_{50}$ | 9i GI$_{50}$ | 9j GI$_{50}$ | 9k GI$_{50}$ | 9l GI$_{50}$ |
|---|---|---|---|---|---|---|---|---|---|---|---|---|
| MCF 7 | <0.01 | <0.01 | <0.01 | 0.01 | <0.01 | <0.01 | 0.14 | 0.12 | <0.01 | <0.01 | <0.01 | <0.01 |
| A 2780 | 0.108 | <0.01 | 0.116 | 0.099 | 0.097 | <0.01 | 0.147 | 0.109 | 0.08 | <0.01 | 0.086 | 0.099 |
| Colo 205 | 0.1 | 0.09 | 0.13 | 0.11 | 0.12 | <0.01 | 0.1 | 0.16 | <0.01 | 0.11 | 0.17 | <0.01 |
| Pc 3 | 0.12 | <0.01 | 0.11 | <0.01 | <0.01 | <0.01 | 0.16 | 0.14 | <0.01 | <0.01 | <0.01 | <0.01 |
| SiHa | 0.13 | <0.01 | 0.13 | 0.12 | 0.107 | <0.01 | 0.168 | 0.13 | 0.117 | <0.01 | 0.13 | 0.125 |
| A 549 | 0.13 | 0.12 | <0.01 | <0.01 | 0.105 | <0.01 | <0.01 | 0.12 | <0.01 | <0.01 | <0.01 | <0.01 |

TABLE 8-continued

GI$_{50}$ (concentration in μM) values for the representative compounds 9a-I against human tumour cell lines.

| Cell Type | 9a GI$_{50}$ | 9b GI$_{50}$ | 9c GI$_{50}$ | 9d GI$_{50}$ | 9e GI$_{50}$ | 9f GI$_{50}$ | 9g GI$_{50}$ | 9h GI$_{50}$ | 9i GI$_{50}$ | 9j GI$_{50}$ | 9k GI$_{50}$ | 9l GI$_{50}$ |
|---|---|---|---|---|---|---|---|---|---|---|---|---|
| HOP 62 | 0.1 | <0.01 | 0.11 | <0.01 | <0.01 | <0.01 | 0.16 | 0.1 | 0.11 | <0.01 | 0.11 | 0.11 |
| KB | 0.12 | <0.01 | 0.11 | 0.11 | <0.01 | <0.01 | 0.16 | 0.12 | <0.01 | <0.01 | 0.11 | 0.11 |

TABLE 9

LC$_{50}$ (concentration in μM) values for the representative compounds 9a-I against human tumour cell lines.

| Cell Type | 9a LC$_{50}$ | 9b LC$_{50}$ | 9c LC$_{50}$ | 9d LC$_{50}$ | 9e LC$_{50}$ | 9f LC$_{50}$ | 9g LC$_{50}$ | 9h LC$_{50}$ | 9i LC$_{50}$ | 9j LC$_{50}$ | 9k LC$_{50}$ | 9l LC$_{50}$ |
|---|---|---|---|---|---|---|---|---|---|---|---|---|
| MCF 7 | 1.9 | <0.01 | 0.17 | 2.1 | 0.15 | <0.01 | 2.4 | 2.2 | 0.15 | <0.01 | 2.6 | 0.16 |
| A 2780 | 23 | 0.12 | 2.3 | 2.4 | 2.2 | 0.089 | 2.25 | 2.3 | 2.25 | 0.139 | 2.16 | 2.1 |
| Colo 205 | >10$^2$ | >10$^2$ | >10$^2$ | >10$^2$ | >10$^2$ | >10$^2$ | >10$^2$ | >10$^2$ | >10$^2$ | >10$^2$ | >10$^2$ | >10$^2$ |
| Pc 3 | 28 | 2.4 | 2.3 | 28 | 2.5 | 2.4 | 31 | 2.4 | 0.23 | 2.5 | 26 | 2.1 |
| SiHa | 27.5 | 2.4 | 27 | 26 | 27.8 | 2.5 | 0.311 | 27 | 28.5 | 28 | 27.8 | 28 |
| A 549 | >10$^2$ | >10$^2$ | 33 | >10$^2$ | >10$^2$ | >10$^2$ | >10$^2$ | >10$^2$ | >10$^2$ | >10$^2$ | >10$^2$ | 30 |
| HOP 62 | 27 | 28 | 29 | 27 | 27 | 2.4 | >10$^2$ | 27 | 27 | 2.3 | 25 | 2.5 |
| KB | 2.4 | 2.2 | 26 | 2.3 | 2.3 | 0.18 | >10$^2$ | 0.2 | 28 | 0.2 | 26 | 2 |

The compounds prepared in this invention have shown remarkable cytotixic activity against cancer cell lines. 9a exhibit GI$_{50}$ ranging from 0.13 to <0.01 μM. 9b exhibit GI50 ranging from 0.12 to <0.01 μM, 9c exhibit GI50 ranging from 0.13 to <0.01 μM, 9d exhibit GI50 ranging from 0.12 to <0.01 μM, 9e exhibit GI50 ranging from 0.12 to <0.01 μM, 9f exhibit GI50 <0.01 μM, 9g exhibit GI50 ranging from 0.168 to <0.01 μM, 9h exhibit GI50 ranging from 0.16 to <0.1 μM, 9i exhibit GI50 ranging from 0.117 to <0.01 μM, 9j exhibit GI50 ranging from 0.11 to <0.01 μM, 9k exhibit GI50 ranging from 0.17 to <0.01 μM, 9l exhibit GI50 ranging from 0.125 to <0.01 μM respectively.

Advantages of the Invention

A series of benzothiazole/benzoxazole-pyrrolobenzodiazepine conjugates has been prepared and evaluated for anti cancer activity. Compounds 9a-l exhibited potent anticancer activity against various cancer cell lines indicating that these compounds had the potential for its development as broad spectrum anticancer agents. The thermal denaturation studies showed that these conjugates have better DNA binding ability when compared to DC-81.

The structural variation of benzothiazole/benzoxazole with piperazine moiety has been utilized for DNA binding aspect. Moreover, one of the potent conjugate 9f (IICT-302) of this series has been evaluate for its in vivo efficacy studies against MCF-7 (breast cancer) and PC-3 (prostate cancer) by using Adriamycin as positive control. The in vivo efficacy study of 9f has exhibited less toxicity and good RTV then control adriyamycin indicating the potential use of these molecules in treating cancer.

Scheme 1

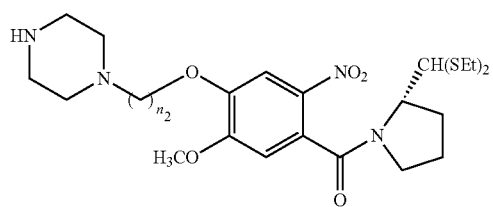

4 a, b
$n = 3, 4$

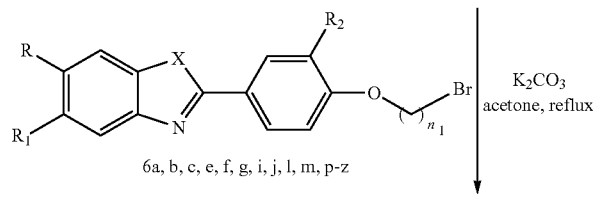

6a, b, c, e, f, g, i, j, l, m, p-z

K$_2$CO$_3$
acetone, reflux

-continued
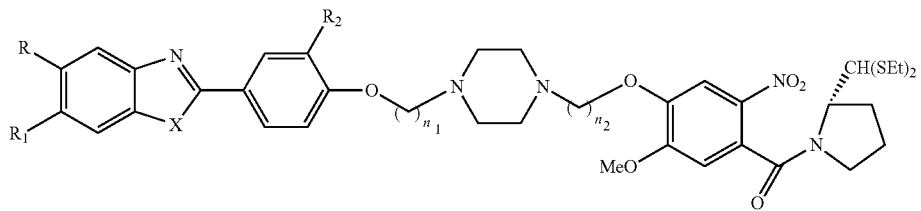
7a, b, c, e, f, g, i, j, l, m, p-z
↓ SnCl$_2$·H$_2$O
methanol, reflux
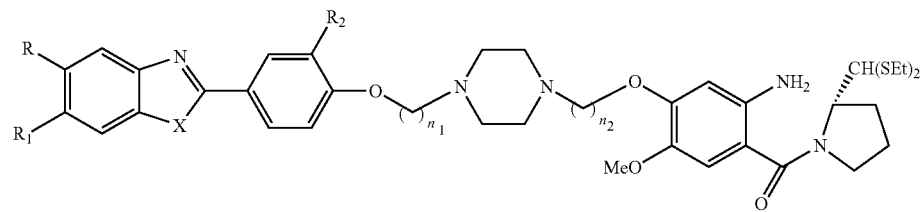
8a, b, c, e, f, g, i, j, l, m, p-z
↓ HgCl$_2$, CaCO$_3$
MeCN, H$_2$O (4:1)
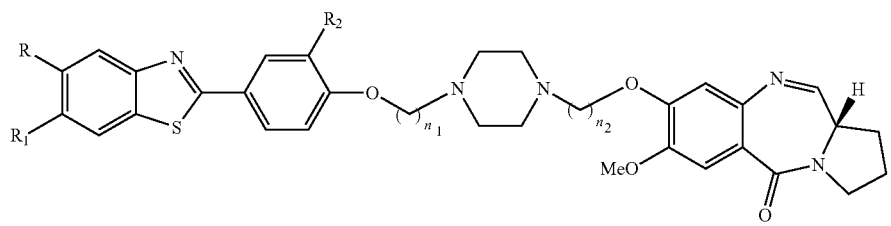
9a, b, c, e, f, g, i, j, l, m, p-z
R, R$_1$ = H, F, CF$_3$, OCF$_3$, Cl, OMe; X = S, O; R$_2$ = H, OMe;
$n_1$ = 3, 4; $n_2$ = 3, 4
Scheme 2
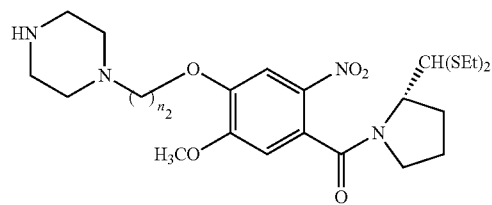
4 a, b
n = 3, 4
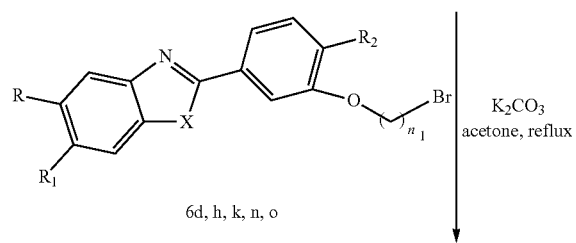
6d, h, k, n, o
K$_2$CO$_3$
acetone, reflux

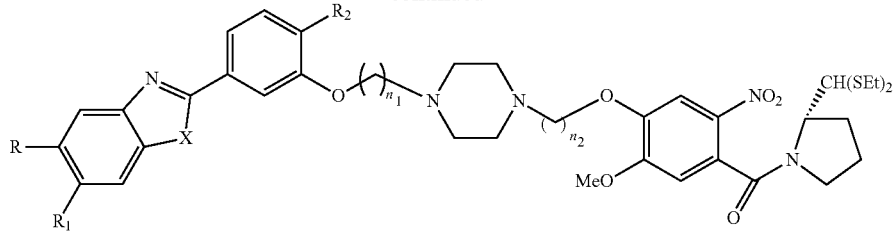
7d, h, k, n, o
↓ SnCl₂·H₂O
methanol, reflux
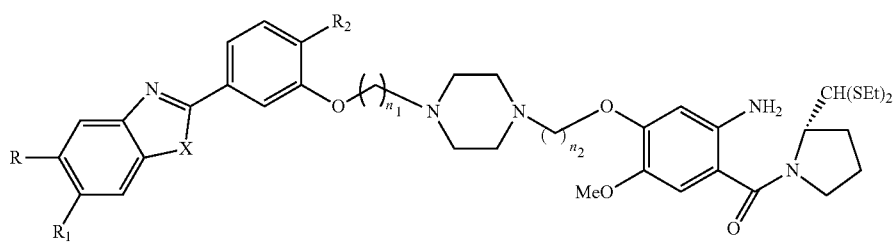
8d, h, k, n, o
↓ HgCl₂, CaCO₃
MeCN, H₂O (4:1)
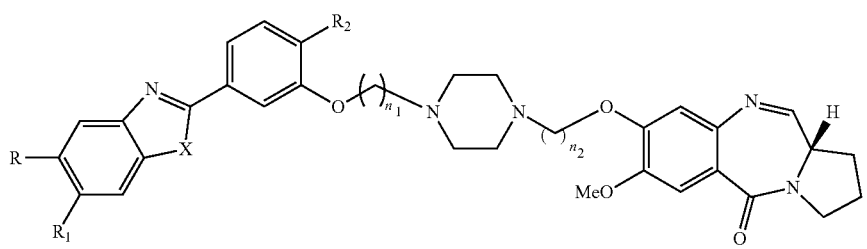
9d, h, k, n, o
R, $R_1$ = H, F, CF₃, OCF₃, Cl, OMe; X = S, O; $R_2$ = H, OMe;
$n_1$ = 3, 4; $n_2$ = 3, 4
We claim:
1. A compound of formula (I):
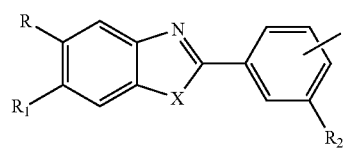
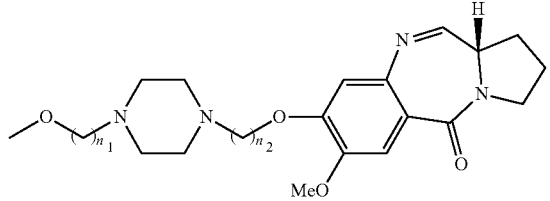
(I) wherein
R, $R_1$ =H, F, OCF₃, CF₃, Cl, or OMe;
$R_2$ =OCH₃ or H;
$n_1$, $n_2$=3 or 4; and
X=S or O.

2. A compound of claim 1, wherein the structural formula of the compound is selected from the group consisting of:
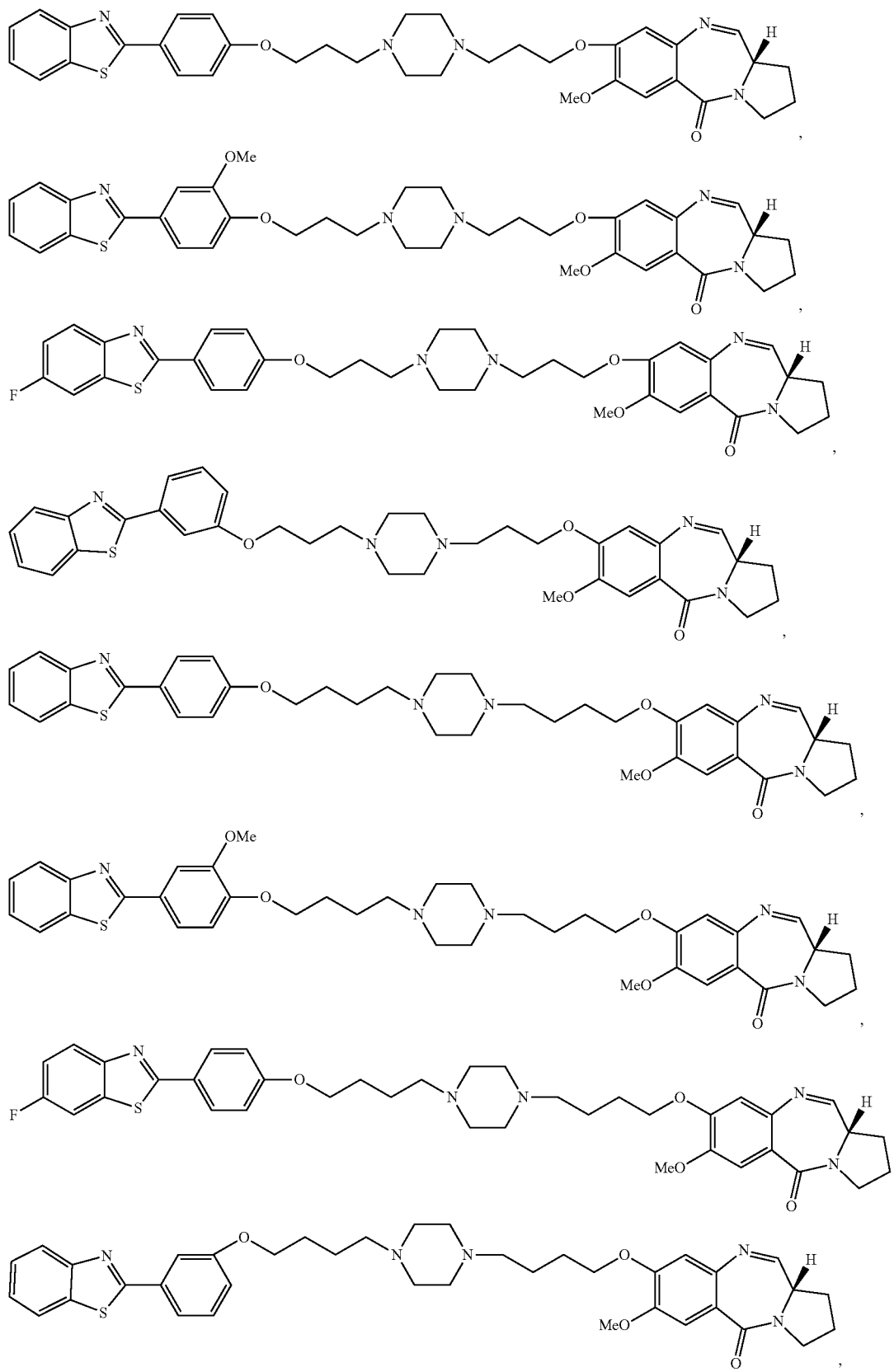

-continued
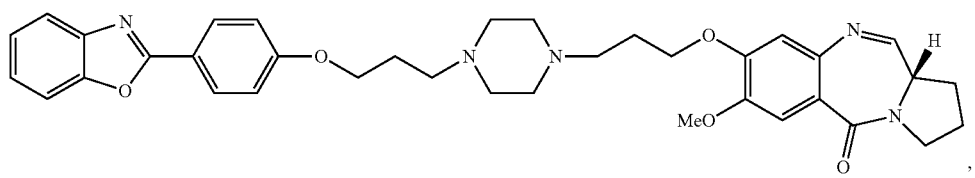
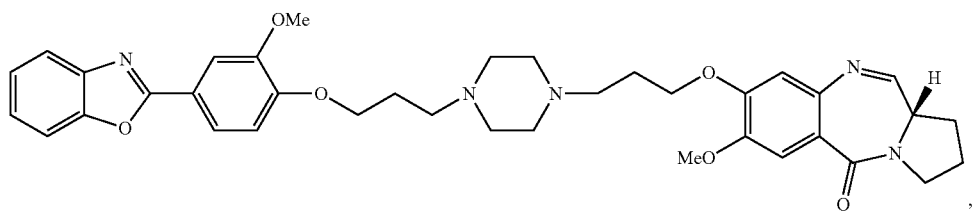
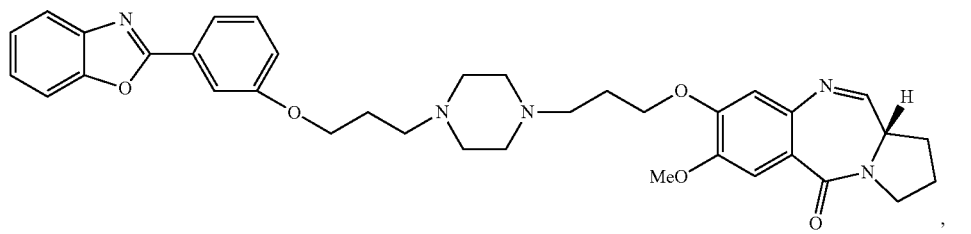
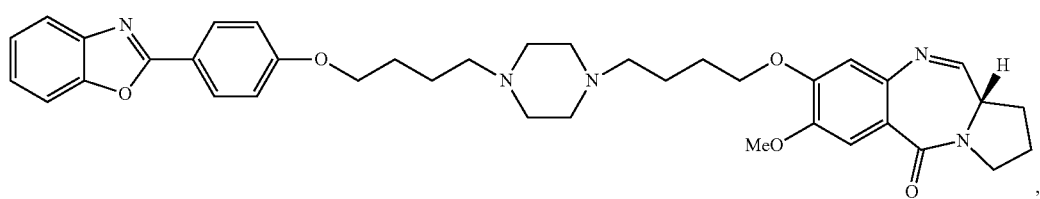
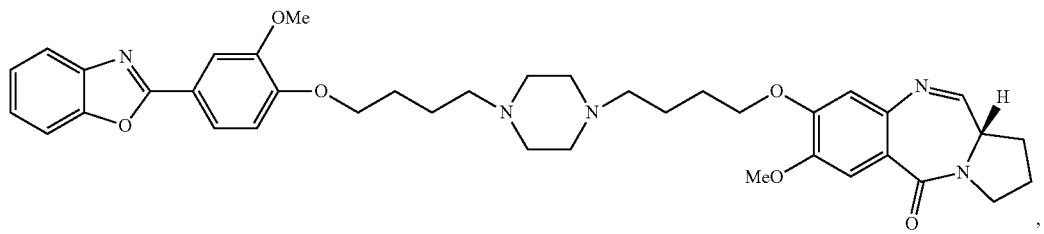
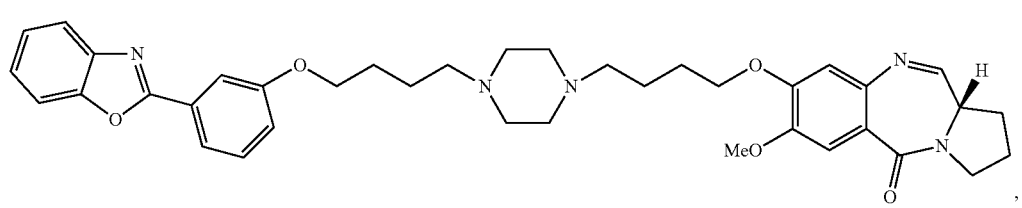
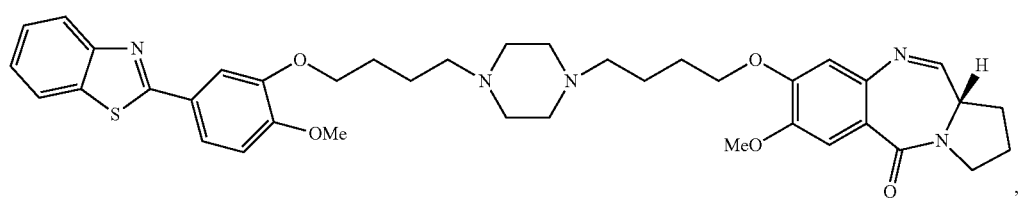
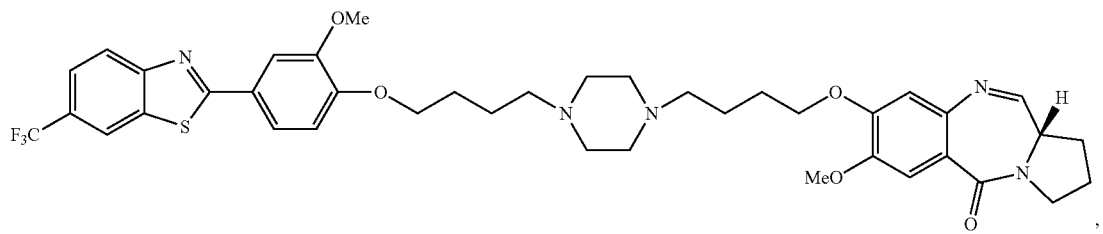

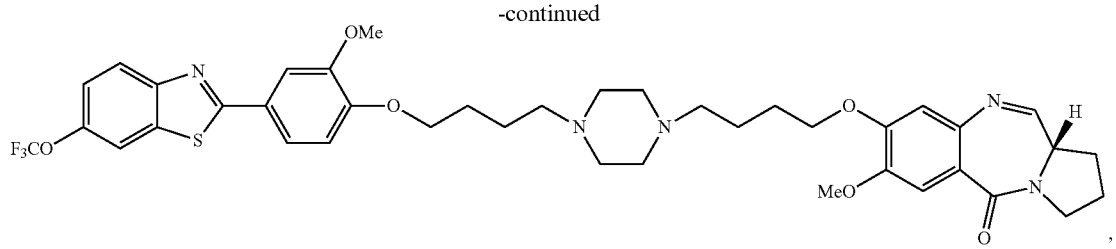,
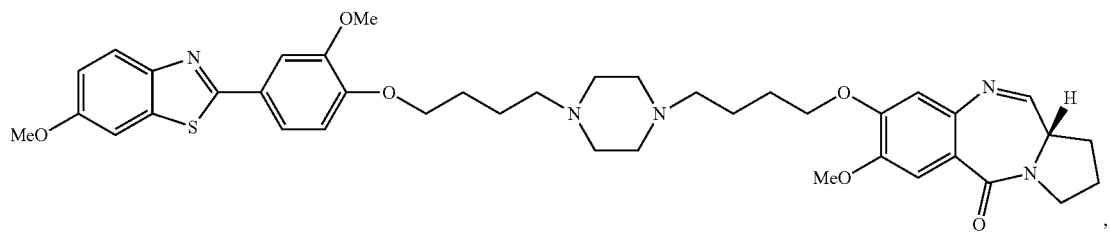,
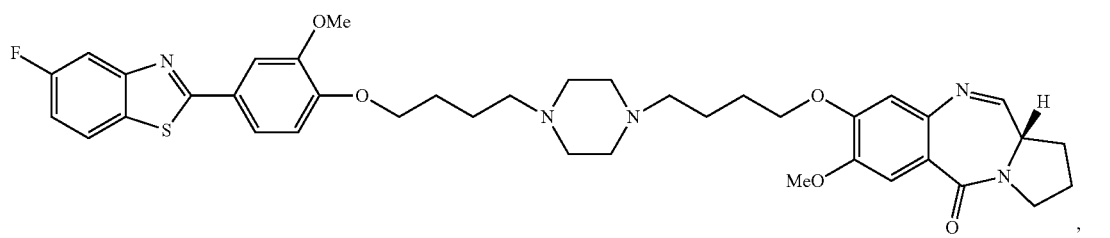,
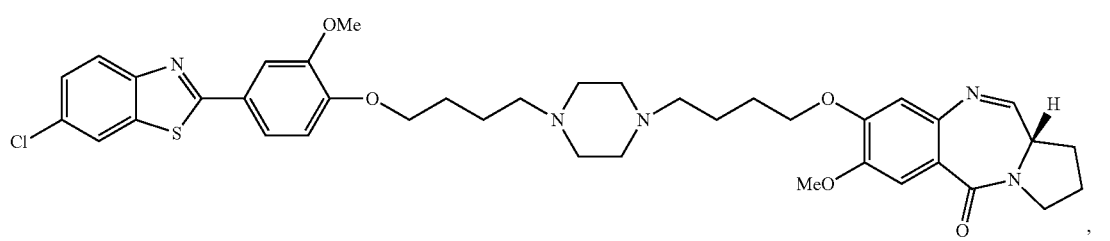,
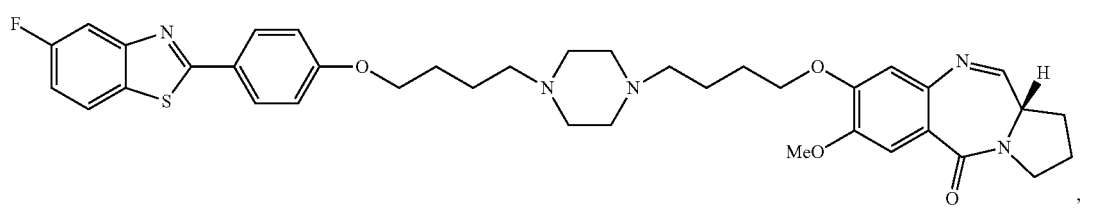,
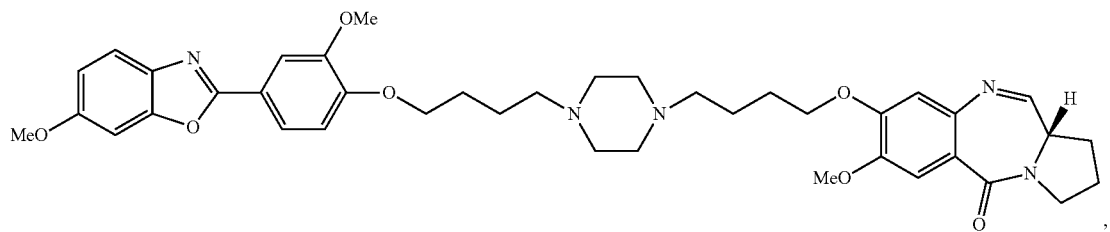,
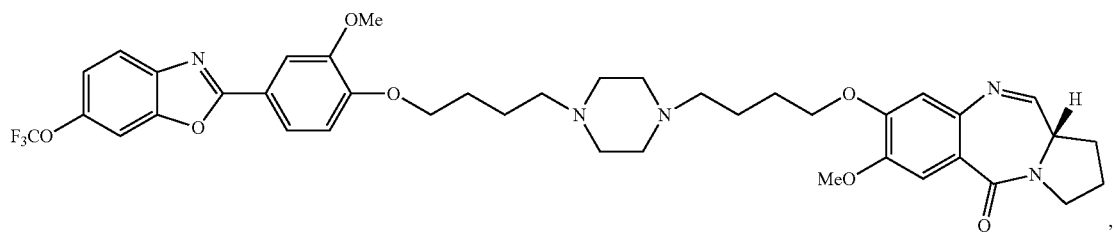,

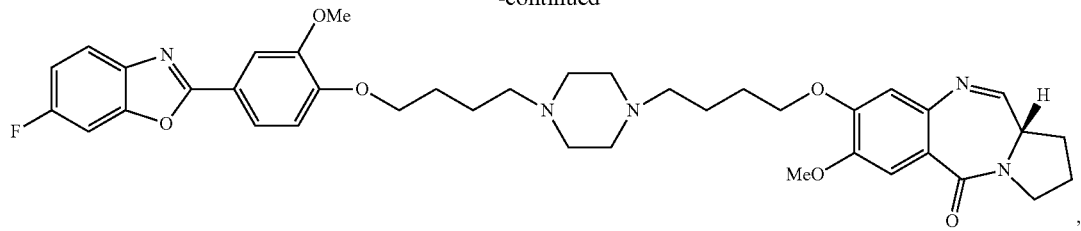

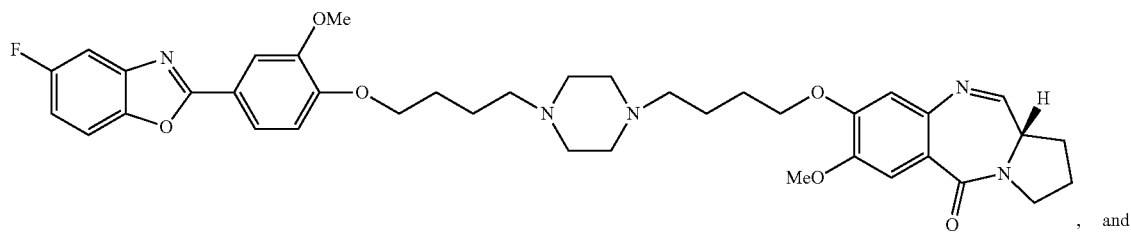, and

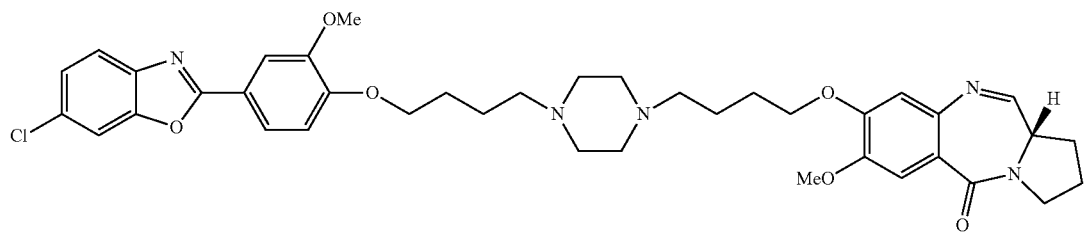

3. A process for the preparation of a compound of claim 1, said process comprising the steps of:

reacting a compound of formula (II), wherein $n_2 = 3$ or 4,

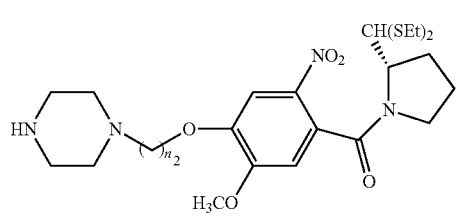

with a benzothiazole or benzoxazole derivative of formula (III) or (IV),

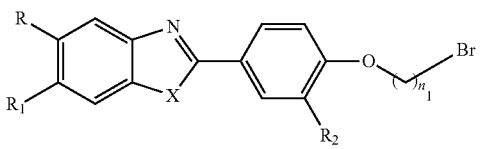

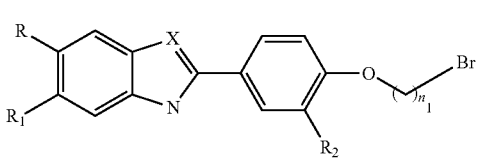

wherein $n_1 = 3$ or 4, R=H or F, $R_1$=H, F, $CF_3$, $OCF_3$, OMe or Cl, $R_2$=H or OMe, and X=S or O, in the presence of $K_2CO_3$, in acetone solvent, under refluxing temperature in the range of 70-75° C. to obtain a resultant nitro compound of formula (V) or (VI),

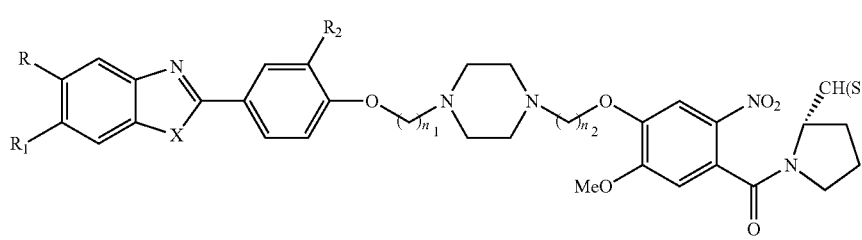

(VI)

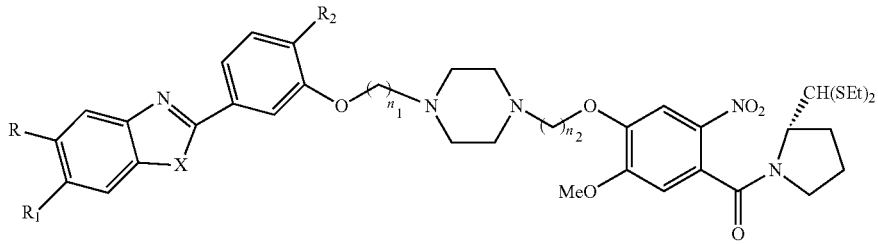

wherein $n_1$ and $n_2$=3 or 4, R=H or F, $R_1$=H, F, $CF_3$, $OCF_3$, OMe or Cl, $R_2$=H or OMe, and X=S or O;

reducing said nitro compound of formula (IV) with $SnCl_2.2H_2O$ in methanol solvent, under reflux temperature in the range of 80-85° C. and isolating a corresponding amino compound of formula (VII) or (VIII), (VII)

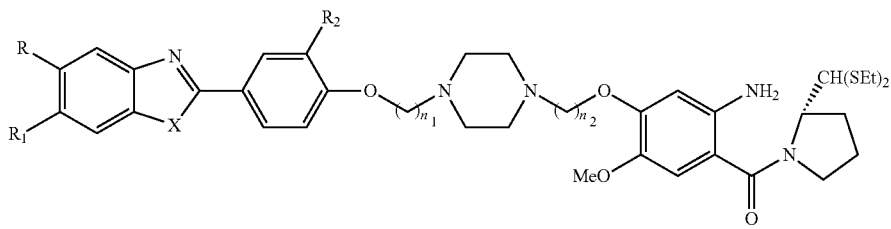

(VIII)

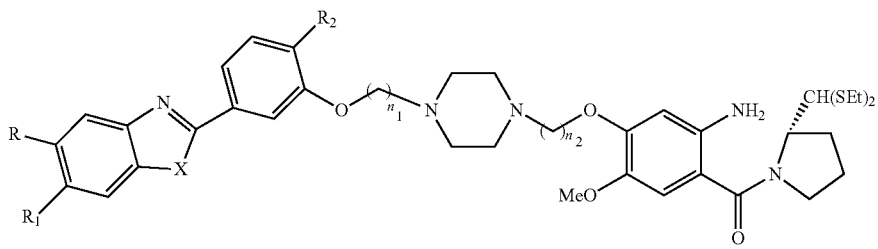

wherein $n_1$ and $n_2$=3 or 4, R=H or F, $R_1$=H, F, $CF_3$, $OCF_3$, OMe or Cl, $R_2$=H or OMe, and X=S or O; and reacting the amino compound of formula (VII) or (VIII) with a deprotecting agent ethanethiol/$BF_3.OEt_2$ to obtain the desired compound of formula (I).

* * * * *